(12) United States Patent
Tetzner et al.

(10) Patent No.: US 7,700,282 B2
(45) Date of Patent: *Apr. 20, 2010

(54) METHOD FOR THE CARRY-OVER PROTECTION IN DNA AMPLIFICATION SYSTEMS TARGETING METHYLATION ANALYSIS ACHIEVED BY A MODIFIED PRE-TREATMENT OF NUCLEIC ACIDS

(75) Inventors: Reimo Tetzner, Berlin (DE); Dimo Dietrich, Berlin (DE)

(73) Assignee: Epigenomics AG, Berlin (DE)

( * ) Notice: Subject to any disclaimer, the term of this patent is extended or adjusted under 35 U.S.C. 154(b) by 64 days.

This patent is subject to a terminal disclaimer.

(21) Appl. No.: 11/248,721

(22) Filed: Oct. 11, 2005

(65) Prior Publication Data

US 2006/0115835 A1 Jun. 1, 2006

Related U.S. Application Data

(60) Provisional application No. 60/618,267, filed on Oct. 12, 2004.

(30) Foreign Application Priority Data

Oct. 11, 2004 (EP) .................................. 04090389

(51) Int. Cl.
  *C12Q 1/70* (2006.01)
  *C12P 19/34* (2006.01)
(52) U.S. Cl. .......................... 435/6; 435/91.1; 435/91.2
(58) Field of Classification Search ........................ None
See application file for complete search history.

(56) References Cited

U.S. PATENT DOCUMENTS

| 5,536,649 | A * | 7/1996 | Fraiser et al. | 435/91.2 |
|---|---|---|---|---|
| 6,369,237 | B1 * | 4/2002 | Verdine et al. | 548/400 |
| 2003/0022215 | A1 | 1/2003 | Makrigiorgos | 435/6 |
| 2003/0148290 | A1* | 8/2003 | Cottrell | 435/6 |
| 2006/0068430 | A1* | 3/2006 | Ward et al. | 435/6 |

FOREIGN PATENT DOCUMENTS

WO WO 03/070986 8/2003

OTHER PUBLICATIONS

Grunau et al. Nucleic Acid Research, 2001, vol. 29, e65, p. 1-7.*
Thomassin, H. et al., Identification of 5-Methylcytosine in Complex Genomes, Methods: A companion to Methods in Enzymology, Academic Press Inc., NY vol. 19:3, Nov. 1999, pp. 465-475.
Kubareva, E.A. et al., Determination of a non-methylated deoxycytidine residue in the ecognition site of DNA-methyltransferases, Biochem 66(12):1356-1360, 2001.
Longo, M.C. et al., Use of uracil DNA glycoslyase to control carry-over contamination in polymerase chain reactions, Gene 93(1):125-128, 1990.
Memisoglu, A. et al., Base excision repair in yeast and mammals, Mutation Research 451(1-2) 39-51, 2000.
Fraga, M.F. et al., DNA Methylation: A profile of methods and applications, Biotechniques, Informa Life Sciences Publishing 33(3):632, 634, 636-649, 2002.
Grigg, G. and Clark, S., Sequencing 5-methylcytosine residues in genomic DNA, Bioessays 16(6):431-436, 1994.
Clark et al., "High sensitivity mapping of methylated cytosines", *Nucleic Acids Research* 22(15):2990-2997, 1994.
Olek et al., "A modified and improved method for bisulphate based cytosine methylation analysis", *Nucleic Acids Research* 24(24):5064-5066, 1996.

* cited by examiner

*Primary Examiner*—Sarae Bausch
(74) *Attorney, Agent, or Firm*—DLA Piper LLP (US)

(57) ABSTRACT

Particular aspects provide methods for specific amplification of template DNA in the presence of potentially contaminating PCR products from previous amplification experiments. Particular embodiments comprise, in a first step, contacting DNA with a bisulfite solution, which sulfonates unmethylated (but not methylated) cytosines, resulting in cytosine deamination and generation of sulfonated uracil. Such sulfonation protects the template nucleic acid from being a target for the enzyme uracil-DNA-glycosylase (UNG), whereas any contaminating DNA, which contains unprotected unsulfonated or desulfonated uracils, is degraded enzymatically while the UNG is active. After UNG treatment and inactivation thereof, the sulfonated uracil bases are converted into uracil by desulfonation. Such aspects have substantial utility for decontamination of nucleic acid samples; e.g., for avoiding amplification of 'carry over products' in the context of DNA methylation analysis. In further aspects, the inventive methods can be generally used as simplified methods of bisulfite treatment.

14 Claims, 5 Drawing Sheets

METHOD FOR THE CARRY-OVER PROTECTION IN DNA AMPLIFICATION SYSTEMS TARGETING METHYLATION ANALYSIS ACHIEVED BY A MODIFIED PRE-TREATMENT OF NUCLEIC ACIDS

FIELD OF THE INVENTION

Aspects relate generally to nucleic acid amplification reactions and more particularly to novel compositions and methods for preventing carry-over contamination within nucleic acid amplification reactions that are directed to methylation analysis.

CROSS-REFERENCE TO RELATED APPLICATIONS

The application claims the benefit of priority to: U.S. Provisional Patent Application Ser. No. 60/618,267, filed 12 Oct. 2004 and entitled A METHOD FOR CARRY-OVER PROTECTION IN DNA AMPLIFICATION SYSTEMS TARGETING METHYLATION ANALYSIS ACHIEVED BY A MODIFIED PRE-TREATMENT OF NUCLEIC ACIDS; and to European Patent Application EP 04 090 389.0, filed 11 Oct. 2004 of same title, both of which are incorporated by reference herein in their entirety.

BACKGROUND

In recent decades, molecular biology studies have focused primarily on genes, the transcription of those genes into RNA, and the translation of the RNA into protein. There has been a more limited analysis of the regulatory mechanisms associated with gene control. Gene regulation, for example, at what stage of development of the individual a gene is activated or inhibited, and the tissue specific nature of this regulation is less well understood. However, such regulation can be with the extent and nature of methylation of the gene or genome. Specific cell types can be correlated with specific methylation patterns, as has been shown for a number of cases (Adorjan et al. (2002) Tumour class prediction and discovery by microarray-based DNA methylation analysis. *Nucleic Acids Res.* 30 (5) e21).

In higher order eukaryotes, DNA is methylated nearly exclusively at cytosines located 5' to guanine in the CpG dinucleotide. This modification has important regulatory effects on gene expression, especially when involving CpG rich areas, known as CpG islands located in the promoter regions of many genes. While almost all gene-associated islands are protected from methylation on autosomal chromosomes, extensive methylation of CpG islands has been associated with transcriptional inactivation of selected imprinted genes and genes on the inactive X-chromosome of females.

Cytosine modification, in form of methylation, contains significant information. The identification of 5-methylcytosine in a DNA sequence, as opposed to unmethylated cytosine; that is, the methylation status, is of great importance and warrants further study. However, because 5-methylcytosine behaves like cytosine in terms of hybridization preference (a property relied on for sequence analysis), its positions/status can not be identified by a normal sequencing reaction. Furthermore, in any amplification, such as a PCR amplification, this relevant epigenetic information, methylated cytosine or unmethylated cytosine, will be lost completely.

Several methods are known in the art that relate to this problem. Usually genomic DNA is treated with a chemical or enzyme leading to a conversion of the cytosine bases, which consequently allows subsequent base differentiation. The most common methods are: a) the use of methylation sensitive restriction enzymes capable of differentiating between methylated and unmethylated DNA; and b) the treatment with a bisulfite reagent. The use of said enzymes is limited due to the selectivity of the restriction enzyme towards a specific recognition sequence.

Therefore, the specific reaction of bisulfite with cytosine, which, upon subsequent alkaline hydrolysis is converted to uracil (whereas 5-methylcytosine remains unmodified under these conditions) (Shapiro et al. (1970) *Nature* 227: 1047) is currently the most frequently used method for analyzing DNA for 5-methylcytosine. Uracil corresponds to thymine in its base pairing behaviour; that is, it hybridizes to adenine; whereas 5-methylcytosine does not change its chemical properties under this treatment, and therefore still has the base pairing behavior of a cytosine (hybridizing with guanine). Consequently, the original DNA is converted in such a manner that 5-methylcytosine, which originally could not be distinguished from cytosine by its hybridization behavior, can now be detected as the only remaining cytosine using standard molecular biological techniques, for example, amplification and hybridization or sequencing. All of these techniques are based on base pairing, which can now thereby be more fully exploited. Comparing the sequences of the DNA with and without bisulfite treatment allows an easy identification of those cytosines that have been unmethylated. An overview of further known methods for detecting 5-methylcytosine may be gathered from the following review article: Fraga & Esteller, *Biotechniques* 33:632, 634, 636-49, 2002.

Again, because the use of methylation-specific enzymes is restricted to certain sequences (comprising restriction sites), most typical methods are based on a bisulfite treatment that is conducted before a detection or amplifying step (for review: DE 100 29 915, A1 p.2, lines 35-46 or the according translated U.S. application Ser. No. 10/311,661, see also WO 2004/067545). The term 'bisulfite treatment' in this context is meant to comprise treatment with a bisulfite, a disulfite or a hydrogensulfite solution. As known to a person or ordinary skill in the art (and as used herein), the term "bisulfite" is used interchangeably for "hydrogensulfite".

Several bisulfite-based protocols are known in the art. However, all of the described protocols, comprise the following steps: the genomic DNA is isolated, denatured, converted several hours by a concentrated bisulfite solution and finally desulfonated and desalted (see, e.g., Frommer et al.: A genomic sequencing protocol that yields a positive display of 5-methylcytosine residues in individual DNA strands. *Proc Natl Acad Sci USA.* 89:1827-31, 1992).

Recent technical improvements of bisulfite methods. The art-recognized agarose bead method incorporates the DNA to be investigated in an agarose matrix, through which diffusion and renaturation of the DNA is prevented (bisulfite reacts only on single-stranded DNA) and all precipitation and purification steps are replaced by rapid dialysis (Olek A. et al. A modified and improved method for bisulphite based cytosine methylation analysis, *Nucl. Acids Res.* 24, 5064-5066, 1996).

Patent application WO 01/98528 (20040152080) describes a bisulfite conversion in which the DNA sample is incubated with a bisulfite solution of a concentration range between 0.1 mol/l to 6 mol/l in the presence of a denaturing reagent and/or solvent and at least one scavenger. In said patent application, several suitable denaturing reagents and scavengers are described. Desulfonation of the deaminated nucleic acid is afforded by incubation of the solution under alkaline conditions.

Patent application WO 03/038121 (US 20040115663) discloses a method in which the DNA to be analysed is bound to a solid surface during the bisulfite treatment. Consequently, purification and washing steps are facilitated.

Patent application WO 04/067545 discloses a method in which the DNA sample is denatured by heat and incubated with a bisulfite solution of a concentration range between 3 mol/l to 6.25 mol/l. Thereby the pH value is between 5.0 and 6.0 and the nucleic acid is deaminated. Deaminated nucleic acids are desulfonated by incubation of the solution under alkaline conditions.

The art-recognized understanding that a 'bisulfite conversion' typically comprises a desulfonation step is illustrated in WO 04/067545:

"According to the invention the term a "bisulfite reaction", "bisulfite treatment" or "bisulfite method" shall mean a reaction for the conversion of a cytosine base, preferably cytosine bases, in a nucleic acid to an uracil base, preferably uracil bases, in the presence of bisulfite ions whereby preferably a 5-methyl-cytosine base, preferably 5-methyl-cytosine bases, is not significantly converted. This reaction for the detection of methylated cytosines is described in detail by Frommer et al., supra and Grigg and Clark (Grigg, G. and Clark, S., *Bioessays* 16:431-436, 1994). The bisulfite reaction contains a deamination step and a desulfonation step, which can be conducted separately or simultaneously (see FIG. 1; Grigg and Clark, supra). The statement that 5-methyl-cytosine bases are not significantly converted shall only take the fact into account that it cannot be excluded that a small percentage of 5-methyl-cytosine bases is converted to uracil although it is intended to convert only and exclusively the (non-methylated) cytosine bases (Frommer et al., supra). The expert skilled in the art knows how to perform the bisulfite reaction, e.g. by referring to Frommer et al., supra or Grigg and Clark, supra who disclose the principal parameters of the bisulfite reaction."

Moreover, WO 04/067545 describes the general state of the art with regard to the different protocols:

"From Grunau et al., supra, it is known to the expert in the field what variations of the bisulfite method are possible. In summary, in the deamination step a buffer containing bisulfite ions, optionally chaotropic agents and optionally further reagents as an alcohol or stabilizers as hydroquinone are employed and the pH is in the acidic range. The concentration of bisulfite is between 0.1 and 6 M bisulfite, preferably between 1 M and 5.5 M, the concentration of the chaotropic agent is between 1 and 8 M, whereby preferably guanidinium salts are employed, the pH is in the acidic range, preferably between 4.5 and 6.5, the temperature is between 0° C. and 90° C., preferably between room temperature (25° C.) and 90° C., and the reaction time is between 30 min and 24 hours or 48 hours or even longer, but preferably between 1 hour and 24 hours. The desulfonation step is performed by adding an alkaline solution or buffer as e.g. a solution only containing a hydroxide, e.g. sodium hydroxide, or a solution containing ethanol, sodium chloride and sodium hydroxide (e.g., 38% EtOH, 100 mM NaCl, 200 mM NaOH) and incubating at room temperature or elevated temperatures for several min, preferably between 5 min and 60 min."

Desulfonation is, therefore, an inherent feature of all of these methods, and in any case a desulfonation takes place before the nucleic acids are used as templates for amplification reactions, in order to provide an ideal template for the polymerase utilized in subsequent reactions.

Patent application WO 05/038051 describes improvements for the conversion of unmethylated cytosine to uracil by treatment with a bisulfite reagent. According to this method the reaction is carried out in the presence of 10-35% by volume, preferentially in the presence of 20-30% by volume of dioxane, one of its derivatives or a similar aliphatic cyclic ether. The bisulfite reaction can also be carried out in the presence of a n-alkylene glycol compound, particularly in the presence of their dialkyl ethers, and especially in the presence of diethylene glycol dimethyl ether (DME). These compounds can be present in a concentration of 1-35% by volume, preferentially of 5-25% by volume. The bisulfite conversion is conducted at a temperature in the range of 0-80° C. and that the reaction temperature is increased for 2 to 5 times to a range of 85-100° C. briefly during the course of the conversion (thermospike). It is further preferred that the temperature increases to 85-100° C., in particular to 90-98° C. during the temperature increase of brief duration.

Subsequent to a bisulfite treatment, usually short, specific fragments of a known gene are amplified and either completely sequenced (Olek A, Walter J, The pre-implantation ontogeny of the H19 methylation imprint. Nat Genet. 3:275-6, 1997) or individual cytosine positions are detected by a primer extension reaction (Gonzalgo M L and Jones P A., Rapid quantitation of methylation differences at specific sites using methylation-sensitive single nucleotide primer extension (Ms-SNuPE). *Nucleic Acids Res.* 25:2529-31, 1997; WO 95/00669) or by enzymatic digestion (Xiong Z, Laird P W., COBRA: a sensitive and quantitative DNA methylation assay. Nucleic Acids Res. 25: 2535-4, 1997).

Another technique to detect hypermethylation is the so-called methylation specific PCR (MSP) (Herman J G, Graff J R, Myohanen S, Nelkin B D and Baylin S B., Methylation-specific PCR: a novel PCR assay for methylation status of CpG islands. *Proc Natl Acad Sci U S A*. 93: 9821-6, 1996). The technique is based on the use of primers that differentiate between a methylated and a non-methylated sequence if applied after bisulfite treatment of said DNA sequence. The primer either contains a guanine at the position corresponding to the cytosine in which case it will after bisulfite treatment only bind if the position was methylated. Or the primer contains an adenine at the corresponding cytosine position and therefore only binds to said DNA sequence after bisulfite treatment if the cytosine was unmethylated and has hence been altered by the bisulfite treatment so that it hybridizes to adenine. With the use of these primers, amplicons can be produced specifically depending on the methylation status of a certain cytosine and will as such indicate its methylation state.

Another technique is the detection of methylation via a labeled probe, such as used in the so called Taqman™ PCR, also known as MethyLight™ (U.S. Pat. No. 6,331,393). With this technique it became feasible to determine the methylation state of single or of several positions directly during PCR, without having to analyze the PCR products in an additional step.

Additionally, detection by hybridization has also been described (Olek et al., WO 99/28498).

The treatment with bisulfite (or similar chemical agents or enzymes) with the effect of altering the base pairing behaviour of one type of cytosine specifically, either the methylated or the unmethylated, thereby introducing different hybridisation properties, makes the treated DNA more applicable to the conventional methods of molecular biology, especially the polymerase based amplification methods, such as the PCR.

Base excision repair. Base excision repair occurs in vivo to repair DNA base damage involving relatively minor disturbances in the helical DNA structure, such as deaminated, oxidized, alkylated or absent bases. Numerous DNA glycosylases are known in the art, and function in vivo during base excision repair to release damaged or modified bases by cleavage of the glycosidic bond that links such bases to the sugar phosphate backbone of DNA (Memisoglu, Samson, Mutation Res., 451:39-51, 2000). All DNA glycosylases cleave glycosidic bonds but differ in their base substrate specificity and in their reaction mechanisms.

Carry-over contamination of amplification reactions (e.g., PCR); inadequacy of the prior art. One widely recognized application of such glycosylases is decontamination in PCR applications. In any such PCR amplification, 2 to the 30 ($2^{30}$) or more copies of a single template are generated. This very large amount of DNA produced helps in the subsequent analysis, like in DNA sequencing according to the Sanger method, but it can also become a problem when this amount of DNA is handled in an analytical laboratory. Even very small reaction volumes, when inadvertently not kept in a closed vial, can lead to contamination of the whole work environment with a huge number of DNA copies. These DNA copies may be templates for a subsequent amplification experiment performed, and the DNA analysed subsequently may not be the actual sample DNA, but contaminating DNA from a previous experiment. This may also lead to positive negative controls that should not contain any DNA and therefore no amplification should be observed.

In practice, this problem can be so persistent that whole laboratories may move to a new location, because contamination of the work environment makes it impossible to still carry out meaningful PCR based experiments. In a clinical laboratory, however, the concern is also that contaminating DNA may cause false results when performing molecular diagnostics. This would mean that actually contaminating DNA that stems from a previous patient is analyzed, instead of the actual sample to be investigated.

Therefore, measures have been implemented to avoid contamination. This involves, for example, a PCR amplification and detection in one tube in a real time PCR experiment. In this case, it is not required that a PCR tube be opened. After use, the tube will be kept closed and discarded and therefore the danger of contamination leading to false results is greatly reduced.

In addition, molecular means exist that reduce the risk of contamination. In a polymerase chain reaction, the enzyme uracil-DNA-glycosylase (UNG) reduces the potential for false positive reactions due to amplicon carryover (see e.g. U.S. Pat. No. 5,035,996 or Thornton C G, Hartley J L, Rashtchian A., Utilizing uracil DNA glycosylase to control carry-over contamination in PCR: characterization of residual UDG activity following thermal cycling. *Biotechniques*, 13:1804, 1992). The principle of this contamination protection method is that in any amplification instead of dTTP dUTP is provided and incorporated and the resulting amplicon can be distinguished from its template and any future sample DNA by uracil being present instead of thymine. Prior to any subsequent amplification, uracil DNA-glycosylase (UNG) is used to cleave these bases from any contaminating DNA, and therefore only the legitimate template remains intact and can be amplified. This method is considered the standard method of choice in the art and is widely used in DNA based diagnostics. The following is a citation from a publication that summarizes the use of UNG (Longo M C, Berninger M S, Hartley J L., Use of uracil DNA glycosylase to control carry-over contamination in polymerase chain reactions. *Gene.*, 93:125-8, 1990):

"Polymerase chain reactions (PCRs) synthesize abundant amplification products. Contamination of new PCRs with trace amounts of these products, called carry-over contamination, yields false positive results. Carry-over contamination from some previous PCR can be a significant problem, due both to the abundance of PCR products, and to the ideal structure of the contaminant material for re-amplification. We report that carry-over contamination can be controlled by the following two steps: (i) incorporating dUTP in all PCR products (by substituting dUTP for dTTP, or by incorporating uracil during synthesis of the oligodeoxyribonucleotide primers; and (ii) treating all subsequent fully preassembled starting reactions with uracil DNA glycosylase (UNG), followed by thermal inactivation of UNG. UNG cleaves the uracil base from the phosphodiester backbone of uracil-containing DNA, but has no effect on natural (i.e., thymine-containing) DNA. The resulting apyrimidinic sites block replication by DNA polymerases, and are very labile to acid/base hydrolysis. Because UNG does not react with dUTP, and is also inactivated by heat denaturation prior to the actual PCR, carry-over contamination of PCRs can be controlled effectively if the contaminants contain uracils in place of thymines."

Another method for carry over protection in PCR has been described by Walder et al (Walder R Y, Hayes J R, Walder J A., Use of PCR primers containing a 3-terminal ribose residue to prevent cross-contamination of amplified sequences. *Nucleic Acids Res.*, 21:4339-43, 1993). Walder et al describe that carry over protection can be achieved—however not very reproducibly—by using primers consisting of a 3'-end which is characterized as a ribo-cytidine. After primer extension the amplification product is cleaved specifically at the site of this ribonucleotide by an enzyme known as RNase A. That way the potentially contaminating amplificates are shortened at their ends and cannot serve a templates for said primers in the following amplification procedure. However, a significant disadvantage inherent to this method is the instability of the primer molecules, containing a ribonucleotide at the 3'-end.

All of the documents cited herein are hereby incorporated by reference in its entirety.

Substantial problem in the prior art. Because the existence of uracils is an inherent feature of bisulfite converted DNA and the necessary property relied upon for detecting methylation differences, the prior art method of choice for carry over protection based on uracil-DNA-glycosylase enzyme activity, as described above, cannot be applied. This limitation is very unfortunate, because a number of powerful assays for diagnosis are based on PCR performed on bisulfite converted DNA as a template. The difficulty of solving the problem for decontamination of bisulfite converted templates is considered a general one, that can not be solved by adaptation of the standard UNG method, as any bisulfite converted DNA will contain uracil as well. It has therefore commonly been argued that, in any uracil-DNA-glycosylase step, the template DNA would be destroyed along with any contaminating DNA.

Therefore, there is a pronounced need in the art for new methods for carry over prevention that have utility for routine performance of such assays. There is a pronounced need in the art to provide solutions to the problem of how to achieve a reliable carry over protection when analysing methylation of cytosine positions in DNA from patient samples.

SUMMARY OF ASPECTS OF THE INVENTION

Presently, no method has been reported to decontaminate DNA samples that would be compatible with bisulfite treated DNA employed as the template for an amplification procedure like PCR. In preferred aspects of the present invention, novel methods are provided to render the most commonly used method, based on use of the glycosylase enzyme UNG as described above, applicable to DNA methylation analysis.

Surprisingly, the instant inventors were able to solve the problem of providing reliable carry-over protection in the context of methylation assays. Preferred aspects comprise sulfonating, or sulfonating and deaminating unmethylated cytosines, without a subsequent desulfonation. After the unmethylated cytosines are converted to C6-sulfonated uracils, the reaction mixture is treated with uracil-DNA-glycosylase (UNG), which degrades all nonsulfonated-uracil-containing DNA and hence every contaminating DNA, but has no effect on the sulfonated-uracil-containing DNA. In particular aspects, a deactivation of the UNG followed by a desulfonation of the sulfonated uracils is carried out.

The discovery, reported upon for the first time in aspects of this application, that sulfonation of uracil at the C6 position protects the uracil from being degraded by UNG, provides a new and surprising solution to the above stated problem. Particular embodiments of the present invention, therefore, comprise methods that provides both a sufficient and reliable differentiation between methylated and unmethylated cytosines, as well as the applicability, in the context of methylation analysis, of the gold standard of carry over protection (based on use of UNG) for common PCR based assays.

Particular aspects disclose methods for the specific amplification of template DNA in the presence of potentially contaminating PCR products from previous amplification experiments. This template DNA is usually derived from isolating the genomic DNA to be analyzed before the method can be applied. Also, the template nucleic acid used in this method is usually already denatured and therefore present in a single stranded modus. In a first step of this representative embodiment, DNA is contacted with a bisulfite solution, which reacts with unmethylated cytosines but not with methylated cytosines, by sulfonating them. This results in a modification of said nucleic acids, which is known as sulfonation. This sulfonation of unmethylated cytosine in aqueous solution results in deamination of the cytosine whereby sulfonated uracil is generated.

It has herein, for the first time, been recognized that such sulfonation (which occurs only at the unmethylated cytosine bases) protects the template nucleic acid from being a target for the enzyme UNG, and thereby allows for discrimination of template nucleic acid and potentially contaminating nucleic acids. Any contaminating DNA, which contains unprotected unsulfonated or desulfonated uracils while UNG is active, is subsequently degraded enzymatically and only the template nucleic acid from the sample remains to be amplified in the next step.

After treatment with UNG has been accomplished and UNG activity is terminated, the sulfonated uracil bases, which replace the unmethylated cytosines, are converted into uracil by desulfonation. The method is useful for decontamination of nucleic acid samples, or for example, for avoiding amplification of 'carry over products,' and in particular in the context of DNA methylation analysis.

Particular aspects provide a method for providing a decontaminated template nucleic acid for polymerase based amplification reactions suitable for DNA methylation analysis, comprising: incubating nucleic acids with a bisulfite reagent solution, whereby the unmethylated cytosines within said nucleic acid are sulfonated, or sulfonated and deaminated, and mixing the sulfonated or sulfonated and deaminated template nucleic acid with the components required for a polymerase mediated amplification reaction or an amplification based detection assay; adding to this mixture UNG and incubating the mixture, whereby nucleic acids containing nonsulfonated uracil are degraded, and terminating UNG activity and desulfonating the template nucleic acid, thereby converting unmethylated deaminated and sulfonated cytosines, i.e. sulfonated uracils into uracils.

In additional embodiments, a polymerase based amplification or amplification based assay is subsequently performed, which preferably takes place in the presence of dUTPs instead of dTTPs.

Preferably, the polymerase activity is started during desulfonation step.

DETAILED DESCRIPTION

Presently, no method has been reported to decontaminate DNA samples that would be compatible with bisulfite treated DNA employed as the template for an amplification procedure like PCR. In preferred aspects of the present invention, novel methods are provided to render the most commonly used method, based on use of the glycosylase enzyme UNG as described above, applicable to DNA methylation analysis.

Particular embodiments provide for a method comprising the following steps:

first, incubating a template nucleic acids with a bisulfite reagent containing solution, whereby the unmethylated cytosines within said nucleic acid are sulfonated, or sulfonated and deaminated;

second, mixing the sulfonated, or sulfonated and deaminated, template nucleic acid with the components required for a polymerase mediated amplification reaction or an amplification based detection assay;

third, adding to this mixture UNG units and incubating said mixture, whereby any nucleic acids containing non-sulfonated uracils are degraded, whereas sulfonated uracils essentially remain intact; and fourth, terminating the UNG activity, and desulfonating the template nucleic acid.

Figure 1:
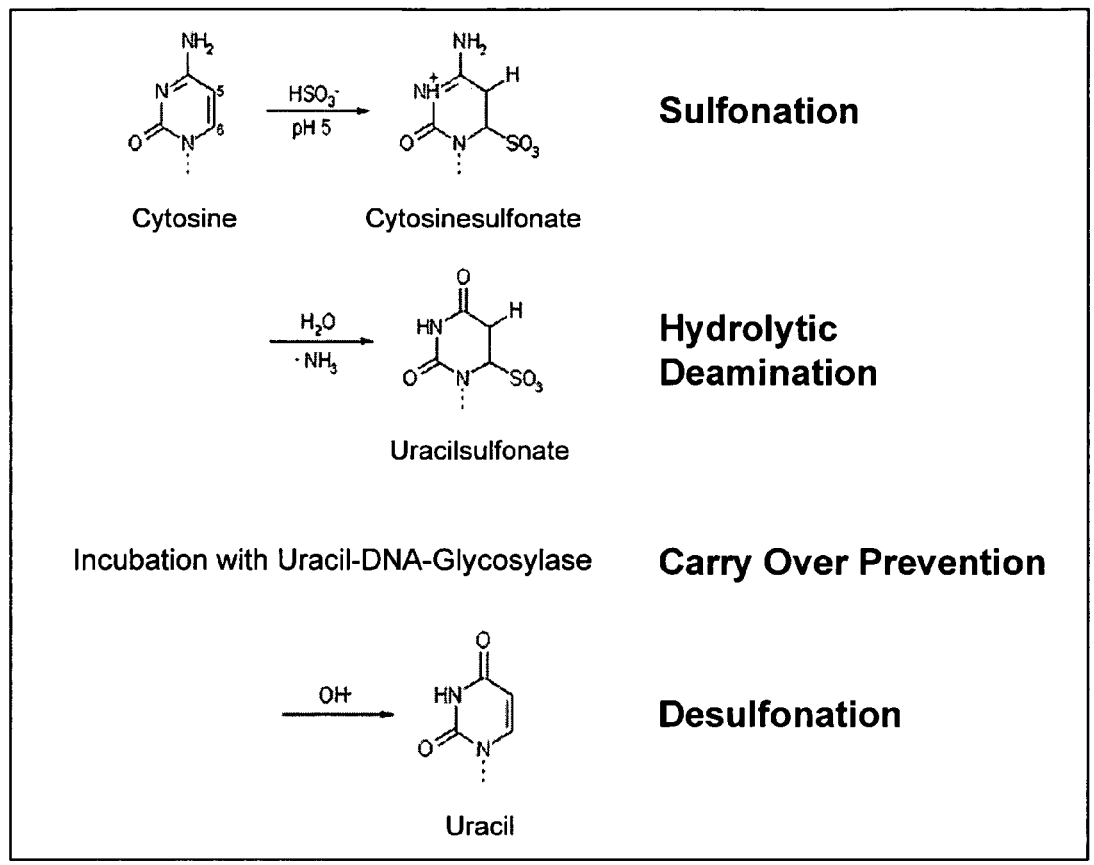
FIG. 1 describes the complete conversion of unmethylated cytosine to uracil, so called bisulfite conversion. The first step of this reaction takes place when unmethylated cytosine bases are contacted with hydrogensulfite at a ph around 5. The sulfonation takes place at position 6 of the cyclic molecule (C6 position). The second step is the deamination that takes place rather spontaneously in aqueous solution and thereby converts cytosine sulfonate into uracil sulfonate. The third step is the desulfonation step, which takes place in alkaline conditions, resulting in uracil.

The sulfonation takes place at C6 position of the base cytosine (FIG. 1). Deamination of sulfonated cytosines takes place spontaneously in aqueous solution, and thereby the sulfonated cytosine is converted into a sulfonated uracil.

Particular aspects are based on two essential discoveries. Firstly, applicants determined that sulfonated nucleic acids are stable up to at least 6 days at 4° C.; e.g., when stored in a common laboratory fridge. This discovery was essential to the method according to the invention because a spontaneous uncontrolled desulfonation of the nucleic acids would render the method unreliable and unstable. Whereas, discovering and knowing that the nucleic acid's sulfonation pattern, basically resembling the nucleic acids methylation pattern, will remain stable when stored for several days at a lower temperature allows the use of this feature in performing sensitive assays to detect exactly which nucleic acids were methylated within a given sample to which extent.

Secondly, it was discovered by applicants that uracil-DNA-glycosylase (UNG) does not degrade nucleic acids containing sulfonated uracils; in other words sulfonated uracils are not a substrate for UNG activity, and therefore are protected from degradation by UNG.

It was also determined by applicants that "real time PCR" assays using sulfonated nucleic acids as template performed well in the presence of UNG activity, indicating that sulfonated nucleic acids as derived from the first step of the bisulfite treatment can serve as templates in PCR based assays.

Additionally, applicants determined that the desulfonation reaction, which must take place before the nucleic acid can be amplified by a polymerase mediated amplification, can be performed within the PCR reaction.

The developed methods, according to particular exemplary aspects of the invention, were successfully tested for GSTP1 and connexine (see Examples herein).

In the first step, the bisulfite mediated cytosine sulfonation may be initiated according to the first steps of common bisulfite conversion protocols as indicated above, in particular as indicated in WO 05/038051 (incorporated by reference herein). The reaction may take place both in solution as well as also on DNA bound to a solid phase. Preferably sodium disulfite (=sodium bisulfite/sodium metabisulfite) is used, since it is more soluble in water than sodium sulfite. The disulfite salt disproportionates in aqueous solution to the hydrogen sulfite anions necessary for the cytosine sulfonation. When bisulfite concentration is discussed in more detail, this refers to the concentration of hydrogen sulfite and sulfite anions in the reaction solution. For the method according to the invention, concentration ranges of 0.1 to 6 mol/l are possible. Particularly preferred is a concentration range of 1 to 6 mol/l, and most particularly preferred, 2-4 mol/l. However, when dioxane is used as a denaturing agent, the maximal working concentration of bisulfite is smaller. Dioxane may also be utilized in different concentrations. Preferably, the dioxane concentration amounts to 10 to 35%, particularly preferred is 20 to 30%, and most particularly preferred is 22 to 28%, especially 25%.

In particularly preferred embodiments with a dioxane concentration of 22-28%, the final preferred bisulfite concentration amounts to 3.3 to 3.6 mol/l, and in the most particularly preferred embodiment with a dioxane concentration of 25%, it amounts to 3.5 mol/l (see Examples).

In another preferred embodiment, DME is used as denaturing agent in different concentrations. DME is used in concentrations in the range of 1-35%, preferable in the range of 5-25%, and most preferably 10%.

In a particularly preferred embodiment the bisulfite conversion is carried out in the presence of scavengers. The preferred scavengers are chromane derivatives, e.g., 6-hydroxy-2,5,7,8,-tetramethylchromane 2-carboxylic acid (also known as: Trolox-C™). Further scavengers are listed in the patent application WO 01/98528 (=DE 100 29 915; =U.S. application Ser. No. 10/311,661; incorporated herein in its entirety).

The bisulfite conversion can be conducted in a wide temperature range from 0 to 95° C. However, in a preferred embodiment the reaction temperature lies between 30-70° C. Particularly preferred is a range between 45-60° C.; most particularly preferred between 50-55° C. The optimal reaction time of the bisulfite treatment depends on the reaction temperature. The reaction time normally amounts to between 1 and 18 hours (see: Grunau et al. 2001, Nucleic Acids Research; 29(13):E65-5.). The preferred reaction time is 4-6 hours for a reaction temperature of 50° C.

In a particularly preferred embodiment of the method according to the invention, the bisulfite conversion is conducted at mild reaction temperatures, wherein the reaction temperature is then clearly increased for a short time at least once during the course of the conversion. The temperature increases of short duration are named "thermospikes" below. The "standard" reaction temperature outside the thermospikes is denoted as the basic reaction temperature. The basic reaction temperature amounts to between 0 and 80° C., preferably between 30-70° C., most preferably 45°-55° C., as described above. The reaction temperature during a thermospike is increased to over 85° C. by at least one thermospike. The optimal number of thermospikes is a function of the basic reaction temperature. The higher the optimal number of thermospikes is, the lower is the basic reaction temperature. In such embodiments, at least one thermospike is necessary in each case. And, on the other hand, in principle, any number of thermospikes is conceivable.

In a particular embodiment, the preferred number of thermospikes is between 1 and 10 thermospikes, depending on the basic reaction temperature. Two to five thermospikes are particularly preferred. During the thermospikes the reaction temperature increases preferably to 85 to 100° C., particularly preferably to 90-98° C., and most preferably to 94° C.-96° C. The duration in time of the temperature increases also depends on the volume of the reaction batch. The duration in time of the thermospikes also depends on the volume of the reaction batch. It must be assured that the temperature is increased uniformly throughout the total reaction solution. For a 20 μl reaction batch when using a thermocycler a duration between 15 seconds and 1.5 minutes, especially a duration between 20 and 50 seconds is preferred. In a particular preferred embodiment the duration is 30 seconds. Operating on a volume of 100 μl the preferred range lies between 30 seconds and 5 minutes, especially between 1 and 3 minutes. Particularly preferred are 1.5 minutes. For a volume of 600 μl, a duration of 1 to 6 minutes is preferred, especially between 2 and 4 minutes. Particularly preferred is a duration of 3 minutes. A person skilled in the art will easily be able to determine suitable durations of thermospikes in relation to a variety of reaction volumes.

The above described use of thermospikes leads to a significantly better conversion rates in the bisulfite conversion reaction, even when the above-described denaturing solvents are not utilized. According to additional aspects of the invention, a method for bisulfite conversion of DNA is hereby characterized in that the basic reaction temperature amounts to 0° C. to 80° C. and that the reaction temperature is increased for a short time to over 85° C. at least once in the course of the conversion.

In the second step, prior to any desulfonation step, units of an enzyme activity, which specifically degrades non-sulfonated uracil containing nucleic acids, are added to said premix. In a preferred embodiment, this degrading enzyme is a DNA-glycosylase or an endonuclease, in particularly UNG (uracil-DNA-glycosylase). The contaminating nucleic acid is characterized, for example, in that it contains non-sulfonated uracil bases. The added degrading enzyme is characterized by cleaving the non-sulfonated uracil base from the phosphodiester backbone of non-sulfonated uracil-containing nucleic acids, but has no effect on sulfonated-uracil containing nucleic acid or on thymine containing nucleic acid, that does not contain uracil. The resulting apyrimidinic sites block replication by DNA polymerases, and are very labile to acid/base hydrolysis.

In another preferred embodiment, the first step is carried out as described above. Thereafter, in an intermediate step, the sulfonated and/or deaminated nucleic acid is mixed with components required for a polymerase mediated amplification reaction or an amplification based detection assay. The amplification reaction mix is prepared according to standard protocols. Such an amplification mix, preferably a PCR mix, may contain at least one primer set of two primers and a polymerase. This polymerase preferably is a heat stable enzyme, even more preferred is the use of a thermally activated polymerase for hot start PCR, and most particularly preferred a thermally activated Taq polymerase is used.

The following second step is also carried out as described above. Units of an enzyme activity, which specifically degrades sulfonated-uracil containing nucleic acid, are added to said premix. The sulfonated sample nucleic acid and a set of at least two primer oligonucleotides are incubated with a composition of enzymes, including an enzyme with sulfonated-uracil containing nucleic acid degrading activity and buffers to cleave or degrade any contaminating nucleic acid. The contaminating nucleic acid is characterized in that it contains uracil bases. The added degrading enzyme activity is characterized by cleaving the uracil base from the phosphodiester backbone of non-sulfonated uracil containing nucleic acid, but has no effect on sulfonated uracil containing nucleic acid or on thymine containing nucleic acid, that does not contain uracil. The resulting apyrimidinic sites block replication by DNA polymerases, and are very labile to acid/base hydrolysis. In principle, the enzymatic activity is any enzymatic activity, which causes specifically apyrimidinic sites or one or more nicks adjacent to a non-sulfonated uracil base. In any case this will result in a block of the replication by DNA polymerase.

The primer oligonucleotides will be chosen such that they amplify a fragment of interest. It is particularly preferred that these primers are designed to amplify a nucleic acid fragment of a template nucleic acid sample by means of a polymerase reaction, in particular a polymerase chain reaction, as known in the art. The primer oligonucleotides are therefore designed to anneal to the template nucleic acids to form a double strand, following the Watson-Crick base pairing rules, and the length of these oligonucleotide primers will be selected such that they anneal at approximately the same temperature.

In said second step, an enzyme and the matching buffers are added to achieve cleavage of any present, contaminating amplificates that were generated in any of the preceding experiments. hese amplificates will have the property that they comprise uracil bases instead of thymine bases, if generated in a polymerase reaction providing dUTPs instead of dTTPs. Therefore, not the sample nucleic acid at this step would be recognized and degraded by the enzyme, but only nucleic acids that were generated in preceding amplifications, the contaminating DNA that has to be removed before the next round of amplification.

It is particularly preferred that the enzyme employed in this second step is uracil-DNA-glycosylase (UNG). It is further preferred that said non-sulfonated uracil containing nucleic acid degrading enzyme is thermolabile, in particular the DNA-glycosylase or the Endonuclease are thermolabile, respectively, and most particularly preferred the UNG is thermolabile.

In the third step, after enzymatic degradation, the composition of enzymes and buffer is subsequently inactivated, in that it is not capable of substantially cleaving any product of the subsequent amplification step. The nonsulfonated-uracil-containing nucleic acid degrading enzyme activity is terminated, in particular the DNA-glycosylase activity or the endonuclease activity is terminated, and most particularly preferred the UNG activity is terminated.

After the composition of non-sulfonated uracil containing nucleic acid degrading enzymes and buffer is inactivated, in that it is not capable of substantially degrading any product of the subsequent amplification step, the fourth step is performed; that is, the desulfonation of the template nucleic acids. Prior to the amplification by a polymerase, a fourth step must be conducted, that is the desulfonation of the sulfonated template nucleic. Desulfonation may take place under alkaline conditions (as described in the art). Desulfonation however may also be catalyzed by an increase in temperature under pH conditions as they are common to the PCR reaction.

It is a preferred embodiment of the invention that steps 3 and 4 are conducted simultaneously by a short increase of the incubation temperature of said premix, which results in deactivation of the non-sulfonated uracil containing nucleic acid degrading enzyme on the one hand and in thermal desulfonation of the template nucleic acid, on the other hand. This increase in the incubation temperature can also be suitable to transfer double-stranded DNA into single-stranded form enabling an amplification.

The sample nucleic acid may now be amplified in the next step using the set of primer oligonucleotides and a polymerase, while any cleaved contaminating DNA is essentially not amplified. The sample nucleic acid may be amplified, using a set of primer oligonucleotides and a polymerase, while the cleaved or degraded contaminating nucleic acid cannot be amplified. The amplified products may now be analyzed and the methylation status in the genomic DNA may be deduced from the presence of an amplified product and/or from the analysis of the sequence within the amplified product.

This amplification may be carried out, in a particularly preferred embodiment of the invention, by means of a polymerase chain reaction, but also by other means of DNA amplification known in the art, like TMA (transcription mediated amplification), isothermal amplifications, rolling circle amplification, ligase chain reaction, and others.

In particular embodiments, the generated DNA fragments will then be analyzed, concerning their presence, the amount, or their sequence properties or a combination thereof.

Therefore one embodiment of the invention is a method for providing a decontaminated template nucleic acid for polymerase based amplification reactions suitable for DNA methylation analysis, which is characterized by: firstly, incubating a template nucleic acid with a bisulfite reagent containing solution, whereby the unmethylated cytosines within said nucleic acid are sulfonated and/or deaminated; secondly, mixing the sulfonated and/or deaminated template nucleic acid with the components required for a polymerase mediated amplification reaction or an amplification based detection assay; thirdly, adding to this mixture an enzyme with uracil-DNA-glycosylase activity and incubating the mixture, whereby nucleic acids containing non-sulfonated uracils are degraded; fourthly, terminating the UNG activity; and fifthly, desulfonating the template nucleic acid.

In a preferred embodiment, the method is further characterized by a step 4 and 5 taking place simultaneously, by briefly incubating the mixture at an increased temperature, whereby the UNG activity is terminated, whereby desulfonation of the template nucleic acid takes place, and whereby the DNA is transferred from a double-stranded form into a single-stranded form suitable for amplification.

In a further preferred embodiment, the template nucleic acid is amplified in a subsequent step 6.

It is further preferred that upon termination of the non-sulfonated uracil containing nucleic acid degrading activity and desulfonation of the template nucleic acid, a polymerase based amplification reaction is started and/or an amplification based assay is performed.

It is further preferred that the polymerase based amplification reaction is started by a brief incubation at increased temperature (heat activation).

In a preferred embodiment of the method the polymerase is a heat stable polymerase.

It is particularly preferred that the polymerase mediated amplification or amplification based assay is performed in the presence of dUTPs instead of dTTPs.

In one preferred embodiment, the method is performed by adding an amount of units of the enzyme, which specifically degrades nonsulfonated-uracil-containing nucleic acids; in the second step that is required to degrade essentially all potential contaminating nucleic acids.

It is especially preferred that upon activation of the polymerase enzyme a polymerase based amplification reaction or an amplification based assay is performed.

It is further preferred that upon activation of the polymerase enzyme a polymerase based amplification reaction or amplification based assay is performed in the presence of dUTPs instead of dTTPs.

It is further preferred that this assay is a real time assay.

In a particularly preferred embodiment, the sample DNA is obtained from serum or other body fluids of an individual. Preferably, the DNA samples are obtained from cell lines, tissue embedded in paraffin, for example tissue from eyes, intestine, kidneys, brain, heart, prostate, lungs, breast or liver, histological slides, body fluids and all possible combinations thereof. The term body fluids is meant to comprise fluids such as whole blood, blood plasma, blood serum, urine, sputum, ejaculate, semen, tears, sweat, saliva, lymph fluid, bronchial lavage, pleural effusion, peritoneal fluid, meningal fluid, amniotic fluid, glandular fluid, fine needle aspirates, nipple aspirate fluid, spinal fluid, conjunctival fluid, vaginal fluid, duodenal juice, pancreatic juice, bile, stool and cerebrospinal fluid. It is especially preferred that said body fluids are whole blood, blood plasma, blood serum, urine, stool, ejaculate, bronchial lavage, vaginal fluid and nipple aspirate fluid.

In a particularly preferred embodiment, the chemical treatment is conducted with a bisulfite (=disulfite, hydrogen sulfite). It is again preferred that the chemical treatment is conducted after embedding the DNA in agarose, or that it is conducted in the presence of a denaturing agent and/or a radical scavenger.

The following methylation detection assays are all preferred embodiments of the invention when performed subsequently to the steps of the method according to the invention:

Methylation Assay Procedures. Various methylation assay procedures are known in the art, and can be used in conjunction with the present invention. These assays allow for determination of the methylation state of one or a plurality of CpG dinucleotides (e.g., CpG islands) within a DNA sequence. Such assays involve, among other techniques, DNA sequencing of bisulfite-treated DNA, and a number of PCR based methylation assays, some of them—known as COBRA, MS-SNuPE, MSP, nested MSP, HeavyMethyl and MethyLight—are described in more detail now.

Bisulfite Sequencing. DNA methylation patterns and 5-methylcytosine distribution can be analyzed by sequencing analysis of a previously amplified fragment of the bisulfite treated genomic DNA, as described by Frommer et al. (Frommer et al. Proc. Natl. Acad. Sci. USA 89:1827-1831, 1992). As the bisulfite treated DNA is amplified before sequencing, the amplification procedure according to the invention may be used in combination with this detection method.

Cobra. COBRA analysis is a quantitative methylation assay useful for determining DNA methylation levels at specific gene loci in small amounts of genomic DNA (Xiong &

Laird, Nucleic Acids Res. 25:2532-2534, 1997). Briefly, restriction enzyme digestion is used to reveal methylation-dependent sequence differences in PCR products of sodium bisulfite-treated DNA. Methylation-dependent sequence differences are first introduced into the genomic DNA by standard bisulfite treatment according to the procedure described by Frommer et al. (Proc. Natl. Acad. Sci. USA 89:1827-1831, 1992) or as described by Olek et al (Olek A, Oswald J, Walter J. (1996) Nucleic Acids Res. 24: 5064-6). PCR amplification of the bisulfite converted DNA is then performed using methylation unspecific primers followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. In addition, this technique can be reliably applied to DNA obtained from microdissected paraffin-embedded tissue samples. Typical reagents (e.g., as might be found in a typical COBRA-based kit) for COBRA analysis may include, but are not limited to: PCR primers for specific gene (or methylation-altered DNA sequence or CpG island); restriction enzyme and appropriate buffer; gene-hybridization oligo; control hybridization oligo; kinase labeling kit for oligo probe; and radioactive nucleotides. Additionally, bisulfite conversion reagents may include: DNA denaturation buffer; sulfonation buffer; DNA recovery reagents or kits (e.g., precipitation, ultrafiltration, affinity column); desulfonation buffer; and DNA recovery components. Additionally, restriction enzyme digestion of PCR products amplified from bisulfite-converted DNA is also used, in the method described by Sadri & Homsby (Nucl. Acids Res. 24:5058-5059, 1996). The bisulfite conversion and amplification procedure according to the invention may be used in combination with this detection method.

Ms-SNuPE (Methylation-Sensitive Single Nucleotide Primer Extension).

The Ms-SNuPE technique is a quantitative method for assessing methylation differences at specific CpG sites based on bisulfite treatment of DNA, followed by single-nucleotide primer extension (Gonzalgo & Jones, Nucleic Acids Res. 25:2529-2531, 1997). Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site(s) of interest. Small amounts of DNA can be analyzed (e.g., microdissected pathology sections), and it avoids utilization of restriction enzymes for determining the methylation status at CpG sites. Typical reagents (e.g., as might be found in a typical Ms-SNuPE-based kit) for Ms-SNuPE analysis may include, but are not limited to: PCR primers for specific gene (or methylation-altered DNA sequence or CpG island); optimized PCR buffers and deoxynucleotides; gel extraction kit; positive control primers; Ms-SNuPE primers for specific gene; reaction buffer (for the Ms-SNuPE reaction); and radioactive nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components. The bisulfite conversion and amplification procedure according to the invention may be used in combination with this detection method.

MSP. MSP (methylation-specific PCR) allows for assessing the methylation status of virtually any group of CpG sites within a CpG island, independent of the use of methylation-sensitive restriction enzymes (Herman et al. Proc. Natl. Acad. Sci. USA 93:9821-9826, 1996; U.S. Pat. No. 5,786,146). Briefly, DNA is modified by sodium bisulfite converting all unmethylated, but not methylated cytosines to uracil, and subsequently amplified with primers specific for methylated versus unmethylated DNA. MSP primer pairs contain at least one primer, which hybridizes to a bisulfite treated CpG dinucleotide. Therefore, the sequence of said primers comprises at least one CpG dinucleotide. MSP primers specific for non-methylated DNA contain a 'T' at the 3' position of the C position in the CpG. Preferably, therefore, the base sequence of said primers is required to comprise a sequence having a length of at least 9 nucleotides which hybridizes to the bisulfite converted nucleic acid sequence, wherein the base sequence of said oligomers comprises at least one CpG dinucleotide. MSP requires only small quantities of DNA, is sensitive to 0.1% methylated alleles of a given CpG island locus, and can be performed on DNA extracted from paraffin-embedded samples. Typical reagents (e.g., as might be found in a typical MSP-based kit) for MSP analysis may include, but are not limited to: methylated and unmethylated PCR primers for specific gene (or methylation-altered DNA sequence or CpG island), optimized PCR buffers and deoxynucleotides, and specific probes. The bisulfite conversion and amplification procedure according to the invention may be used in combination with this detection method.

Nested MSP (Belinsky and Palmisano in US application 20040038245). Considering the apparent conflict of requiring high specificity of the MSP primer to sufficiently differentiate between CG and TG positions but allowing for a mismatch in order to create a unique restriction site it is preferred to use an amended version of MSP, known as nested MSP, as described in WO 02/18649 and US patent application 20040038245 by Belinsky and Palmisano. This method to detect the presence of gene-specific promoter methylation, comprises the steps of: expanding the number of copies of the genetic region of interest by using a polymerase chain reaction to amplify a portion of said region where the promoter methylation resides, thereby generating an amplification product; and using an aliquot of the amplification product generated by the first polymerase chain reaction in a second, methylation-specific, polymerase chain reaction to detect the presence of methylation. In other words a non methylation specific PCR is performed prior to the methylation specific PCR. The bisulfite conversion and amplification procedure according to the invention may be used in combination with this detection method.

Heavymethyl™. (WO 02/072880; Cottrell SE et al. Nucleic Acids Res. 2004 Jan 13;32(1):e10) A further preferred embodiment of the method comprises the use of blocker oligonucleotides. In the HeavyMethyl™ assay blocking probe oligonucleotides are hybridized to the bisulfite treated nucleic acid concurrently with the PCR primers. PCR amplification of the nucleic acid is terminated at the 5' position of the blocking probe, such that amplification of a nucleic acid is suppressed where the complementary sequence to the blocking probe is present. The probes may be designed to hybridize to the bisulfite treated nucleic acid in a methylation status specific manner. For example, for detection of methylated nucleic acids within a population of unmethylated nucleic acids, suppression of the amplification of nucleic acids which are unmethylated at the position in question would be carried out by the use of blocking probes comprising a 'CpA' or 'TpA' at the position in question, as opposed to a 'CpG' if the suppression of amplification of methylated nucleic acids is desired. For PCR methods using blocker oligonucleotides, efficient disruption of polymerase-mediated amplification requires that blocker oligonucleotides not be elongated by the polymerase. Preferably, this is achieved through the use of blockers that are 3'-deoxyoligonucleotides, or oligonucleotides derivatized at the 3' position with other than a "free" hydroxyl group. For example, 3'—O—acetyl oligonucleotides are representative of a preferred class of blocker molecule. Additionally, polymerase-mediated decomposition of the blocker oligonucleotides should be precluded. Preferably, such preclusion comprises either use of a polymerase lacking 5'-3' exonuclease activity, or use of modified blocker oligonucleotides having, for example, thioate bridges at the 5'-terminii thereof that render the blocker molecule nuclease-resistant. Particular applications may not require such 5' modifications of the blocker. For example, if the blocker- and primer-binding sites overlap, thereby precluding binding of the primer (e.g., with excess blocker), degradation of the blocker oligonucleotide will be substantially precluded. This is because the polymerase will not extend the primer toward, and through (in the 5'-3' direction) the blocker—a process that normally results in degradation of the hybridized blocker oligonucleotide.

A particularly preferred blocker/PCR embodiment, for purposes of the present invention and as implemented herein, comprises the use of peptide nucleic acid (PNA) oligomers as blocking oligonucleotides. Such PNA blocker oligomers are ideally suited, because they are neither decomposed nor extended by the polymerase. Preferably, therefore, the base sequence of said blocking oligonucleotide is required to comprise a sequence having a length of at least 9 nucleotides which hybridizes to the chemically treated nucleic acid sequence, wherein the base sequence of said oligonucleotides comprises at least one CpG, TpG or CpA dinucleotide. The bisulfite conversion and amplification procedure according to the invention may be used in combination with this detection method.

Preferably, real-time PCR assays are performed specified by the use of such primers according to the invention. Real-time PCR assays can be performed with methylation specific primers (MSP-real time) as methylation-specific PCR ("MSP"; as described above), or with non-methylation specific primers in presence of methylation specific blockers (HM real-time) ("HEAVYMETHYL", as described above). Real-time PCR may be performed with any suitable detectably labelledlabeled probes. For details see below.

Both of these methods (MSP or HM) can be combined with the detection method known as MethyLight™ (a fluorescence-based real-time PCR technique) (Eads et al., Cancer Res. 59:2302-2306, 1999), which generally increases the specificity of the signal generated in such an assay. Whenever the real-time probe used is methylation specific in itself, the technology shall be referred to as MethyLight™, a widely used method.

Another assay makes use of the methylation specific probe, the so called "QM" (quantitative methylation) assay. A methylation unspecific, therefore unbiased real-time PCR amplification is performed which is accompanied by the use of two methylation specific probes (MethyLight™) one for the methylated and a second for the unmethylated amplificate. That way two signals are generated which can be used to a) determine the ratio of methylated (CG) to unmethylated (TG) nucleic acids, and at the same time b) the absolute amount of methylated nucleic acids can be determined, when calibrating the assay with a known amount of control DNA. MethyLight™.

The MethyLight™ assay is a high-throughput quantitative methylation assay that utilizes fluorescence-based real-time PCR (TaqMan™) technology that requires no further manipulations after the PCR step (Eads et al., Cancer Res. 59:2302-2306, 1999). Briefly, the MethyLight™ process begins with a mixed sample of genomic DNA that is converted, in a sodium bisulfite reaction, to a mixed pool of methylation-dependent sequence differences according to standard procedures (the bisulfite process converts unmethylated cytosine residues to uracil). Fluorescence-based PCR is then performed either in an "unbiased" (with primers that do not overlap known CpG methylation sites) PCR reaction, or in a "biased" (with PCR primers that overlap known CpG dinucleotides) reaction. Sequence discrimination can occur either at the level of the amplification process or at the level of the fluorescence detection process, or both.

The MethyLight™ assay may be used as a quantitative test for methylation patterns in the genomic DNA sample, wherein sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe overlie any CpG dinucleotides. Alternatively, a qualitative test for genomic methylation is achieved by probing of the biased PCR pool with either control oligonucleotides that do not "cover" known methylation sites (a fluorescence-based version of the "MSP" technique), or with oligonucleotides covering potential methylation sites.

The MethyLight™ process can by used with a "TaqMan®" probe in the amplification process. For example, double-stranded genomic DNA is treated with sodium bisulfite and subjected to one of two sets of PCR reactions using TaqMan® probes; e.g., with either biased primers and TaqMan® probe, or unbiased primers and TaqMan® probe. The TaqMan® probe is dual-labeled with fluorescent "reporter" and "quencher" molecules, and is designed to be specific for a relatively high GC content region so that it melts out at about 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan®) probe by digesting it to release the fluorescent reporter molecule for quantitative detection of its now unquenched signal using a real-time fluorescent detection system.

Variations on the TaqMan™ detection methodology that are also suitable for use with the described invention include the use of dual-probe technology (LightCycler™) or fluorescent amplification primers (Sunrise™ technology). Both these techniques may be adapted in a manner suitable for use with bisulfite treated DNA, and moreover for methylation analysis within CpG dinucleotides.

Typical reagents (e.g., as might be found in a typical MethyLight™-based kit) for MethyLight™ analysis may include, but are not limited to: PCR primers for specific bisulfite sequences, i.e. bisulfite converted genetic regions (or bisulfite converted DNA or bisulfite converted CpG islands); probes (e.g. TaqMan® or LightCycler™) specific for said amplified bisulfite converted sequences; optimized PCR buffers and deoxynucleotides; and a polymerase, such as Taq polymerase. The bisulfite conversion and amplification procedure according to the invention may be used in combination with this detection method.

The fragments obtained by means of the amplification can carry a directly or indirectly detectable label. Preferred are labels in the form of fluorescence labels, radionuclides, or detachable molecule fragments having a typical mass, which can be detected in a mass spectrometer. Where said labels are mass labels, it is preferred that the labeled amplificates have a single positive or negative net charge, allowing for better detectability in the mass spectrometer. The detection may be carried out and visualized by means of, e.g., matrix assisted laser desorption/ionization mass spectrometry (MALDI) or using electron spray mass spectrometry (ESI).

Matrix Assisted Laser Desorption/Ionization Mass Spectrometry (MALDI-TOF) is a very efficient development for the analysis of biomolecules (Karas & Hillenkamp, Anal Chem., 60:2299-301, 1988). An analyte is embedded in a light-absorbing matrix. The matrix is evaporated by a short laser pulse thus transporting the analyte molecule into the vapour phase in an unfragmented manner. The analyte is ionized by collisions with matrix molecules. An applied voltage accelerates the ions into a field-free flight tube. Due to their different masses, the ions are accelerated at different rates. Smaller ions reach the detector sooner than bigger ones. MALDI-TOF spectrometry is well suited to the analysis of peptides and proteins. The analysis of nucleic acids is somewhat more difficult (Gut & Beck, Current Innovations and Future Trends, 1:147-57, 1995). The sensitivity with respect to nucleic acid analysis is approximately 100-times less than for peptides, and decreases disproportionally with increasing fragment size. Moreover, for nucleic acids having a multiply negatively charged backbone, the ionization process via the matrix is considerably less efficient. In MALDI-TOF spectrometry, the selection of the matrix plays an eminently important role. For desorption of peptides, several very efficient matrixes have been found which produce a very fine crystallization. There are now several responsive matrixes for DNA, however, the difference in sensitivity between peptides and nucleic acids has not been reduced. This difference in sensitivity can be reduced, however, by chemically modifying the DNA in such a manner that it becomes more similar to a peptide. For example, phosphorothioate nucleic acids, in which the usual phosphates of the backbone are substituted with thiophosphates, can be converted into a charge-neutral DNA using simple alkylation chemistry (Gut & Beck, Nucleic Acids Res. 23: 1367-73, 1995). The coupling of a charge tag to this modified DNA results in an increase in MALDI-TOF sensitivity to the same level as that found for peptides.

The amplificates may also be further detected and/or analysed by means of oligonucleotides constituting all or part of an "array" or "DNA chip" (i.e., an arrangement of different oligonucleotides and/or PNA-oligomers bound to a solid phase). Such an array of different oligonucleotide- and/or PNA-oligomer sequences can be characterized, for example, in that it is arranged on the solid phase in the form of a rectangular or hexagonal lattice. The solid-phase surface may be composed of silicon, glass, polystyrene, aluminum, steel, iron, copper, nickel, silver, or gold. Nitrocellulose as well as plastics such as nylon, which can exist in the form of pellets or also as resin matrices, may also be used. An overview of the Prior Art in oligomer array manufacturing can be gathered from a special edition of Nature Genetics (Nature Genetics Supplement, Volume 21, January 1999, and from the literature cited therein). Fluorescently labeled probes are often used for the scanning of immobilized DNA arrays. The simple attachment of Cy3 and Cy5 dyes to the 5'—OH of the specific probe are particularly suitable for fluorescence labels. The detection of the fluorescence of the hybridized probes may be carried out, for example, via a confocal microscope. Cy3 and Cy5 dyes, besides many others, are commercially available. The bisulfite conversion and amplification procedure according to the invention may be used in combination with this detection method.

A particular preferred embodiment of the invention is a method for providing a decontaminated nucleic acid for hybridisation on a DNA-Array, preferably an Oligonucleotide-Array, suitable for DNA methylation analysis.

Of course, a particular preferred embodiment of the invention is also a improved method for bilsulfite conversion of DNA. Thereby non-methylated cytosines are converted to uracil while methylated cytosines remain unchanged. According to this embodiment, a nucleic acid is incubated with a bisulfite reagent containing solution, whereby the unmethylated cytosines within said nucleic acid are sulfonated and/or deaminated but not yet desulfonated as this is described above. Afterwards the sulfonated and/or deaminated template nucleic acid is mixed with components required for a polymerase mediated amplification reaction or an amplification based detection assay. Thereafter the template nucleic acid is desulfonated by briefly incubating the mixture at an increased temperature. Subsequently the desulfonated template nucleic acid is amplified. In a particularly preferred variant the polymerase based amplification reaction is started by a brief incubation at increased temperature (heat activation). Simultaneously, this brief incubation at increased temperature serves to desulfonate the sulfonated and/or deaminated template nucleic acid. Furthermore it is particularly preferred that the polymerase is a heat stable polymerase.

This particular embodiment has the advantage, in comparison to known methods of bisulfite treatment, that the purification step after bisulfite treatment becomes dispensable. This is a simplification which results in reduction of costs and handling effort, minimizes loss of bisulfite treated DNA and is also time-saving. Therefore the use of this embodiment is preferred if DNA samples are treated with bisulfite and subsequently are amplified. This is especially preferred if large amount of samples are analyzed. The use of this embodiment is further preferred with regard to sensitive detection methods for DNA methylation analysis like COBRA, MS-SNuPE, MSP, nested MSP, HeavyMethyl™ and MethyLight™.

Furthermore, the invention regards to a test kit for the realisation of the method according to the invention with a component containing bisulfite, for example a reagent or solution containing bisulfite, and a component containing an enzymatic activity. This enzymatic activity specifically degrades DNA containing non-sulfonated uracil. In particular this enzymatic activity is an activity of a DNA-glycosylase and/or an endonuclease, preferentially this enzymatic activity is an uracil-DNA-glycosylase, and more preferentially this enzymatic activity is uracil-N-DNA-Glycosylase (UNG). The added degrading enzyme activity is characterized by its ability to cause specifically apyrimidinic sites and/or one or more nicks adjacent to a non-sulfonated uracil base. In any case, this will result in a block of the replication by DNA polymerase. In a particular test kit, the enzymatic activity is characterized by cleaving the uracil base from the phosphodiester backbone of non-sulfonated uracil containing nucleic acid, but has no effect on sulfonated uracil containing nucleic acid or on thymine containing nucleic acid, that does not contain uracil. The resulting apyrimidinic sites block replication by DNA polymerases, and are very labile to acid/base hydrolysis.

A further test kit comprises one or more of the additional components. This can be:
- one or more denaturing reagent and/or solution, for example: dioxane or diethylene glycol dimethyl ether (DME) or any substance, which is suitable as described in WO 05/038051;
- one or more scavenger, for example 6-hydroxy-2,5,7,8-tetramethylchromane 2-carboxylic acid or other scavengers as described in WO 01/98528 or WO 05/038051;
- one or more primers, which are suitable for the amplification of one or more DNA amplificates, amongst others the primer or primers can be modified, for example with a quencher and/or a label for detection as well known by a person skilled in the art like the dye FAM or the quencher BHQ black hole or dabcyl;
- one or more probes, which can be any probe, which can be used to specifically record the amplification of one or more amplificates for example in a real-time-assay, amongst others the probe or probes can be modified, for example with a quenscher and/or a label for detection as well known by a person skilled in the art like the dye FAM or the quencher BHQ black hole or dabcyl;
- one or more blockers, which are nucleic acids and can be used to block the binding of a specific primer or the replication by DNA polymerase, amongst others the blocker or blockers can be modified, for example with a quenscher and/or a label for detection as well known by a person skilled in the art like the dye FAM or the quencher BHQ black hole or dabcyl;
- one or more reaction buffers, which are suitable for a bisulfite treatment and/or a PCR reaction,
- nucleotides, which can be dATP, dCTP, dUTP and dGTP or any derivative of these nucleotides,
- $MgCl_2$ as a substance or in solution and/or any other magnesium salt, which can be used to carry out a DNA polymerase replication;
- DNA polymerase, for example Taq polymerase or any other polymerase with or without proof-reading acitivity,—dye or quencher, which can be used for the detection of the amplificates as known in the art, for example an intercalating dye like SYBR Green or a dye for linkage to a primer or probe or blocker like the dye FAM or the quencher BHQ black hole or dabcyl; and/or
- any reagent, solution, device and/or instruction which is useful for realisation of an assay according to the invention.

The methods and test kits disclosed here are preferable used for the diagnosis and/or prognosis of adverse events for patients or individuals, whereby diagnosis means diagnose of a adverse event, a predisposition for a adverse event and/or a progression of a adverse events. hese adverse events belong to at least one of the following categories: undesired drug interactions; cancer diseases; CNS malfunctions, damage or disease; symptoms of aggression or behavioral disturbances; clinical, psychological and social consequences of brain damage; psychotic disturbances and personality disorders; dementia and/or associated syndromes; cardiovascular disease, malfunction or damage; malfunction, damage or disease of the gastrointestinal tract; malfunction, damage or disease of the respiratory system; lesion, inflammation, infection, immunity and/or convalescence; malfunction, damage or disease of the body as an abnormality in the development process; malfunction, damage or disease of the skin, of the muscles, of the connective tissue or of the bones; endocrine and metabolic malfunction, damage or disease; headaches or sexual malfunction.

The methods and test kits also serve in a particularly preferred manner for distinguishing cell types, tissues or for investigating cell differentiation. They serve in a particularly preferred manner for analysing the response of a patient to a drug treatment.

In another preferred manner the methods and test kits of the invention can also be used to characterize the DNA methylation status in that positions are methylated or non-methylated compared to normal conditions if a single defined disease exists. In a particular preferred manner they can serve for identifying an indication-specific target, wherein a template nucleic acid is treated with bisulfite and UNG enzyme activity, and wherein an indication-specific target is defined as differences in the DNA methylation status of a DNA derived from a diseased tissue in comparison to a DNA derived from a healthy tissue. These tissue samples can originate from diseased or healthy patients or from diseased or healthy adjacent tissue of the same patient.

In a particular preferred manner the indication specific target is a protein, peptide or enzyme, and in particular a per se known modulator of the coded protein, peptide or enzyme is assigned with the specific indication of the diseased tissue. In a particular preferred manner this modulator serves for preparing a pharmaceutical composition with a specific indication, in particular a specific cancer indication.

In a particular preferred manner the enzyme UNG serves as an enzyme for generation of contamination free nucleic acids for methylation analysis.

Exemplary Preferred Embodiments:

Particular aspects provide an assay for providing a decontaminated nucleic acid suitable for DNA methylation analysis, comprising: a) contacting a DNA sample with a bisulfite reagent under conditions suitable to produce a bisulfite-treated sulfonated DNA sample, wherein unmethylated cytosines of the DNA are sulfonated, sulfonated and deaminated, or comprise a mixture of both forms, and wherein said sulfonated, or sulfonated and deaminated uracil has not been significantly desulfonated; and b) further contacting the bisulfite-treated sulfonated DNA sample with an amount of an enzyme that specifically degrades any contaminating non-sulfonated-uracil-containing nucleic acids to provide for a decontaminated DNA sample. In particular aspects, the contaminating nonsulfonated-uracil-containing nucleic acids comprise nonsulfonated-uracil-containing carry-over contaminants from a prior nucleic acid amplification reaction, and wherein the decontaminated DNA sample is thereby optimized for use in a subsequent amplification analysis. Preferably, the subsequent amplification analysis comprises DNA methylation analysis.

Additional aspects provide the above methods, further comprising:—mixing the bisulfite-treated sulfonated DNA sample with at least one component required for a polymerase-mediated amplification reaction or an amplification-based detection assay;—inactivating, after specifically degrading any nonsulfonated-uracil-containing nucleic acids, the specifically degrading enzymatic activity; and—desulfonating, after said inactivating, the bisulfite-treated sulfonated DNA sample. In particular embodiments, inactivating and desulfonating occur simultaneously by incubating the mixture at an increased temperature, said incubation sufficient to inactivate the specifically degrading enzymatic activity, and desulfonate the bisulfite-treated sulfonated DNA. Preferably, the method further comprises, after desulfonating, amplifying the desulfonated DNA. In particular embodiments, the specifically degrading enzyme is at least one selected from the group consisting of a DNA glycosylase and an endonuclease. Preferably, the DNA glycosylase is uracil-DNA-glycosylase (UNG).

Additional embodiments further comprise, after inactivating and desulfonating, performing a polymerase-based amplification reaction or an amplification-based assay. In particular aspects, the polymerase-based amplification reaction is initiated by a brief incubation at increased temperature, said incubation sufficient to inactivate the specifically degrading enzymatic activity. Preferably, the polymerase is a heat stable polymerase. In preferred aspects, the polymerase-mediated amplification, or the amplification-based assay is performed in the presence of dUTPs instead of dTTPs.

In preferred embodiments, the amount of the specifically degrading enzyme is sufficient to degrade substantially all of any nonsulfonated-uracil-containing nucleic acid contaminants.

Yet further embodiments provide a method for bisulfite treatment of a nucleic acid, comprising: a) contacting a nucleic acid with a bisulfite reagent under conditions suitable to produce a bisulfite-treated sulfonated nucleic acid sample, wherein unmethylated cytosines of the nucleic acid are sulfonated, sulfonated and deaminated, or comprise a mixture of both forms, and wherein said sulfonated, or sulfonated and deaminated uracil has not been significantly desulfonated; b) further contacting the bisulfite-treated sulfonated nucleic acid sample with at least one component required for a polymerase-mediated amplification reaction or an amplification-based detection assay; and c) desulfonating the bisulfite-treated sulfonated nucleic acid sample by a brief incubation of the mixture at an increased temperature. Particular embodiment of this method further comprise, after desulfonating, amplifying the desulfonated nucleic acid with a polymerase-mediated amplification reaction or an amplification-based detection assay. Preferably, a heat stable polymerase is used. In particular embodiments, the polymerase-based amplification reaction is briefly incubated at an increased temperature to simultaneously start the reaction, and allow for desulfonation of the bisulfite-treated sulfonated nucleic acid sample.

Further aspects provide a kit for decontaminating a nucleic acid sample, comprising: a bisulfite reagent; and an enzymatic activity that specifically degrades nonsulfonated-uracil-containing DNA. Preferably, the enzymatic activity is that of uracil-DNA-glycosylase (UNG). In additional embodiments, the kit further comprises at least one component selected from the group consisting of: denaturing reagent and solution; scavenger; primer; probe; reaction buffer; nucleotides; $MgCl_2$ solution; polymerase, dye for the production of amplificates; and instructions for using the kit.

Additional embodiments provide a method for diagnosis, prognosis, or both of an adverse event for patients or individuals, comprising use of the above described methods or kits, and wherein the adverse event is at least one selected from the group consisting of: undesired drug interactions; cancer diseases; CNS malfunctions; damage or disease; symptoms of aggression or behavioral disturbances; clinical, psychological and social consequences of brain damages; psychotic disturbances and personality disorders; dementia and/or associated syndromes; cardiovascular disease of the gastrointestinal tract; malfunction, damage or disease of the respiratory system; lesion, inflammation, infection, immunity and/or convalescence; malfunction, damage or disease of the body as an abnormality in the development process; malfunction, damage or disease of the skin, of the muscles, of the connective tissue or of the bones; endocrine and metabolic malfunction, damage or disease; headaches and sexual malfunction.

Yet further embodiments provide a method for distinguishing cell types or tissue or for investigating cell differentiation, comprising performing a nucleic acid-based assay suitable for distinguishing cell types or tissue or for investigating cell differentiation, and wherein one or more of the above described methods or kits are used to provide for decontaminated nucleic acid samples.

Additional aspects provide a method for identifying an indication-specific target or marker, comprising performing a suitable DNA methylation assay on DNA of a test sample and determining the methylation status, relative to a normal control status, at one or more positions of the DNA, wherein the determined methylation status is indicative for the presence or absence of a single defined disease, and wherein one or more of the above described methods are used to decontaminate the test sample DNA prior to performing the methylation analysis. In particular embodiments, the methods comprise: treating a test nucleic acid sample with a bisulfite reagent to sulfonate unmethylated cytosines of the nucleic acid; contacting the bisulfite-treated nucleic acid with uracil-DNA-glycosylase (UNG) under conditions suitable to specifically degrade any contaminating nonsulfonated-uracil-containing nucleic acids to provide for a decontaminated nucleic acid sample; and performing a methylation assay on the decontaminated nucleic acid to determine the methylation status, relative to a normal control status, at one or more positions of the DNA, wherein the determined methylation status is indicative for the presence or absence of a single defined disease. In particular aspects, the indication-specific target is a protein, peptide or enzyme. Preferably, a per se known modulator of the coded protein, peptide or enzyme is assigned to the specific indication of the diseased tissue.

Additional aspects provide a method for providing decontaminated nucleic acid suitable for methylation analysis, comprising bisulfite treatment of a nucleic acid sample to provide for a sulfonated nucleic acid sample; and contacting the bisulfite-treated sulfonated nucleic acid sample with uracil-DNA-glycosylase (UNG) under conditions suitable to specifically degrade any contaminating nonsulfonated-uracil-containing nucleic acids to provide for a decontaminated nucleic acid sample suitable for methylation analysis.

EXAMPLE 1

(Amplification of Methylated DNA of the GSTP1 Gene (Also Known as GST-pi Gene) Wherein Human DNA Containing Sulfonated Uracils Served as Template)

The use of uracil-DNA-glycosylase is a method well known in the art to avoid false positive results in polymerase based amplification methods, caused by cross contamination by previously amplified products (Pang J., Mol Cell Probes. 1992 Jun;6(3):251-6). This method is however not applicable for polymerase based amplification methods which have the purpose to detect uracil bases within the given template. This is the case in DNA methylation analysis, wherein one way to detect the difference between methylated and unmethylated cytosines is to mirror these differences into the difference between cytosine and uracil, which is facilitated by the widely spread use of common bisulfite conversion methods. These have the effect to convert unmethylated cytosines into uracils whereas methylated cytosines remain cytosines.

Therefore in subsequent amplification reactions to detect methylation patterns the template contains uracils.

In the following example it was shown that the method according to the invention allows Uracil-DNA-glycosylase (UNG) based technique for carry over prevention of bisulfite converted DNA, without loss of the critical information, which bases were unmethylated and which were methylated. To achieve this the following steps were carried out:

Two nucleic acid samples, containing 1.5 μg GpGenome™ Universal Methylated DNA (Chemicon International) diluted in 100 μl water were mixed with 354 μl of bisulfite solution (5.89 mol/l) and 146 μl of dioxane containing a radical scavenger (6-hydroxy-2,5,7,8-tetramethylchromane 2-carboxylic acid, 98.6 mg in 2.5 ml of dioxane). The reaction mixture was denatured for 3 min at 99° C. and subsequently incubated with the following temperature program for a total of 5 h: 30 min at 50° C.; a first thermospike (99.9° C.) for 3 min; 1.5 h at 50° C.; a second thermospike (99.9° C.) for 3 min; 3 h at 50° C. One of the reaction mixtures served as a control whereas the other was treated according to the invention. The reaction mixtures of both the control and the test reaction were subsequently purified by ultrafiltration by means of a Millipore Microcon column. The purification was conducted essentially according to the manufacturer's instructions. For this purpose, the reaction mixture was mixed with 200 μl of water, loaded onto the ultrafiltration membrane, centrifuged for 15 min and subsequently washed with water. The DNA remains on the membrane in this treatment. For the control sample an alkaline desulfonation was performed according to the methods, which are state of the art (see for example US 20040152080, 20040115663, WO 2004/067545). For this purpose, 100 μl of a 0.2 mol/l NaOH was added and incubated for 10 min. For the other sample this desulfonation step was replaced by adding 100 μl water. A centrifugation (10 min) was then conducted, followed by a final washing step with water. After this, the DNA was eluted. For this purpose, the membrane was mixed for 10 minutes with 50 μl of warm 1×TE buffer (50° C.) adjusted to pH7. The membrane was turned over according to the manufacturer's instructions. Subsequently a repeated centrifugation was conducted, with which the DNA was removed from the membrane.

Subsequently the DNA was stored at 4° C. for 12 h and then used as template in a PCR reaction.

By stopping the chemical reaction after sulfonation all unmethylated cytosines are converted into C6 sulfonated uracils (5,6-Dihydro-6-sulfonyl-uracil) and methylated cytosines remain unchanged. However after a complete desulfonation, as described in the art, all unmethylated cytosines are converted in uracil and methylated cytosines remain unchanged.

Figure 2:
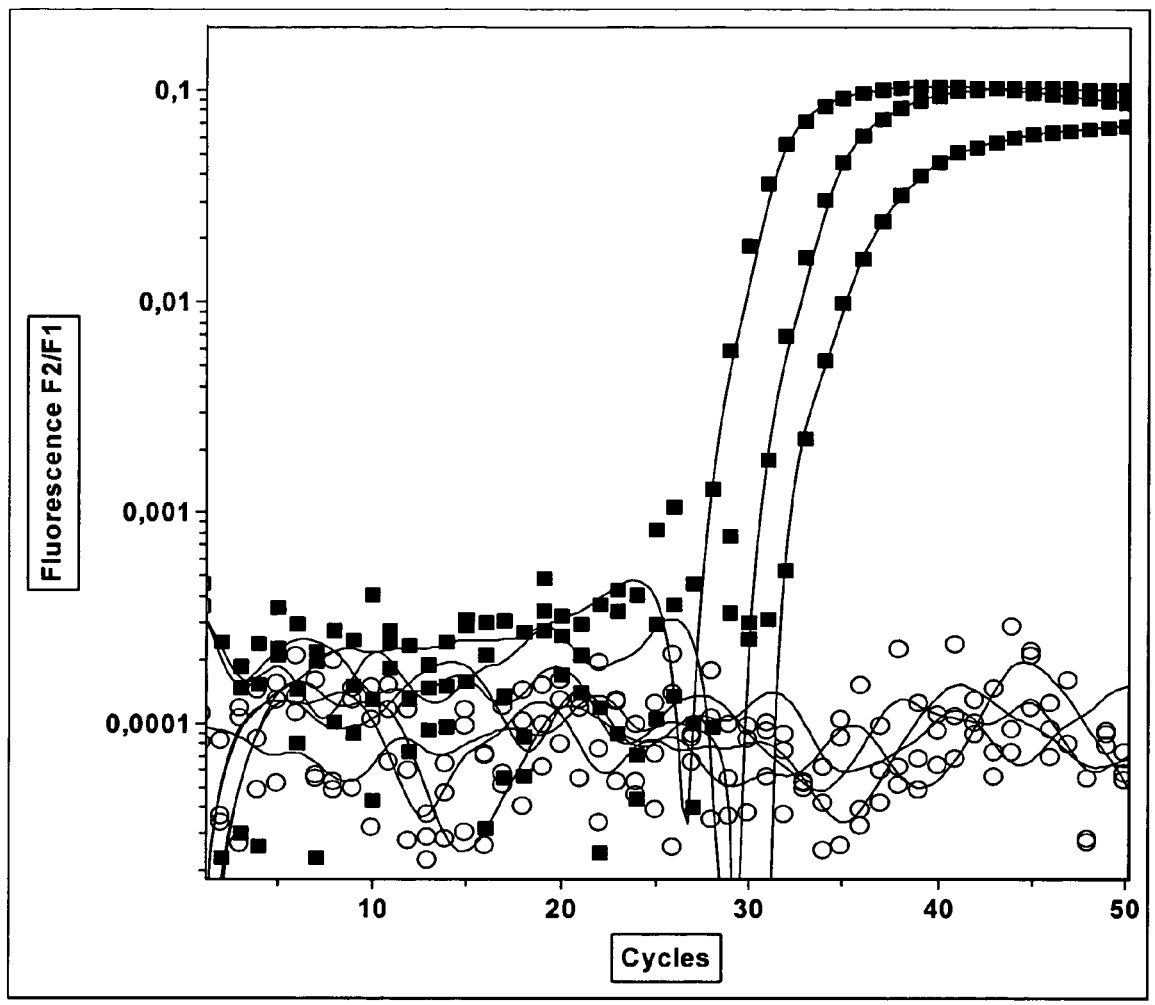
FIG. 2 shows a plot of real time amplification of methylated DNA of the GSTP1 gene from desulfonated bisulfite converted DNA, according to the state of the art. The Y-axis shows the fluorescence signal measured in channel F2 normalized against channel F1 at each cycle (X-axis). 10 ng, 1 ng respective 0.1 ng bisulfite treated methylated DNA were added to the reaction. No signals were determined using the reaction mix containing Uracil-DNA-glycosylase (labeled in open circles) indicating a complete degradation of the bisulfite converted DNA. Amplification occurs only in absence of Uracil-DNA-glycosylase (labeled in rectangles). No template control is marked as solid line.
Figure 3:
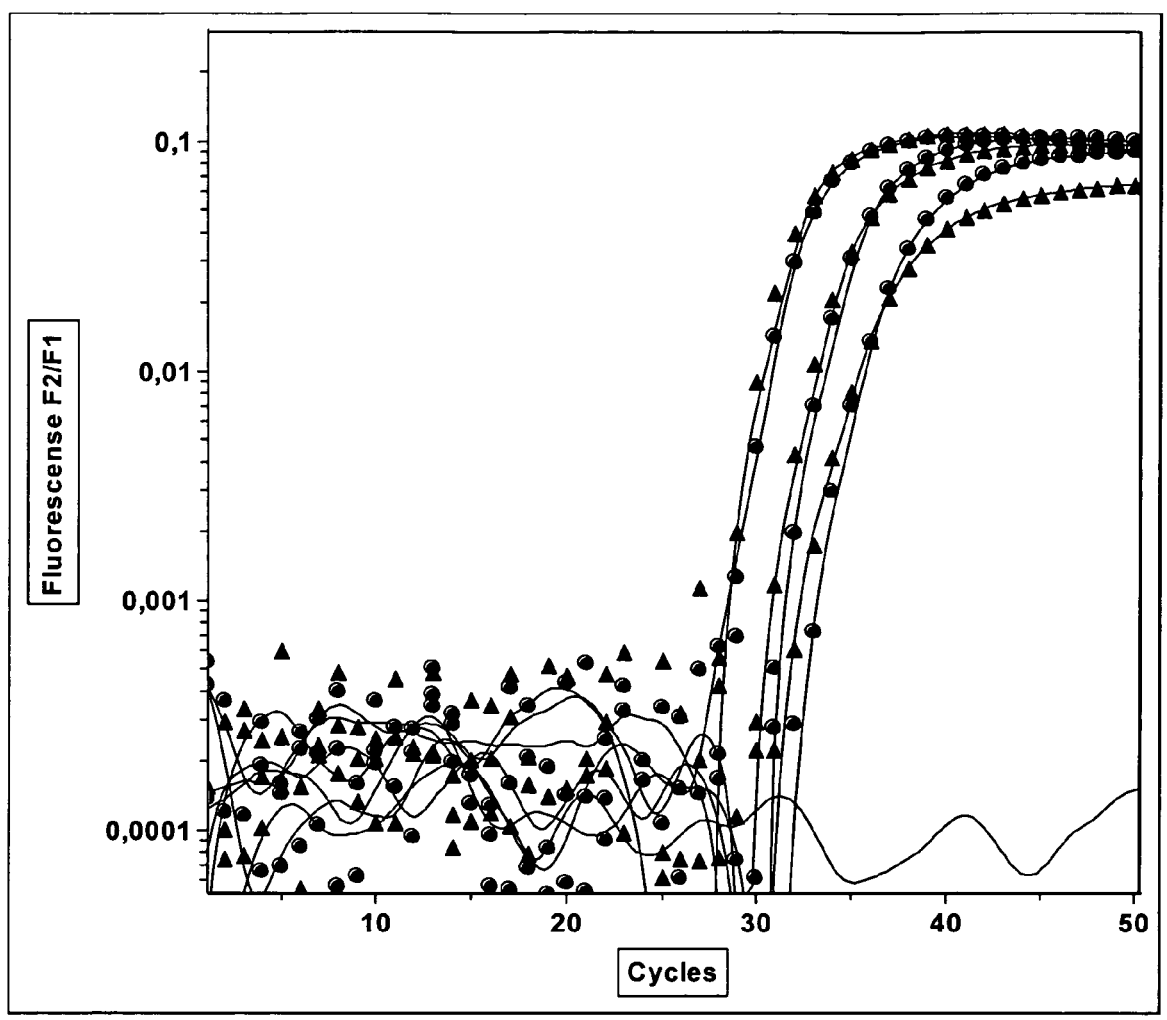
FIG. 3 is a plot of real time amplification of methylated DNA of the GSTP1 gene from bisulfite converted DNA according to the claimed new method without desulfonation. The Y-axis shows the fluorescence signal measured in channel F2 normalized against channel F1 at each cycle (X-axis). 10 ng, 1 ng respective 0.1 ng bisulfite treated methylated DNA were added to the reaction. The signals generated from reaction without Uracil-DNA-glycosylase are labeled with circles. No significant difference in amplification was determined from the reaction containing Uracil-DNA-glycosylases (labeled in triangles) indicating that 6-Sulfon-Uracil containing DNA is not a template for UNG. No template control is marked as solid line.
Figure 4:
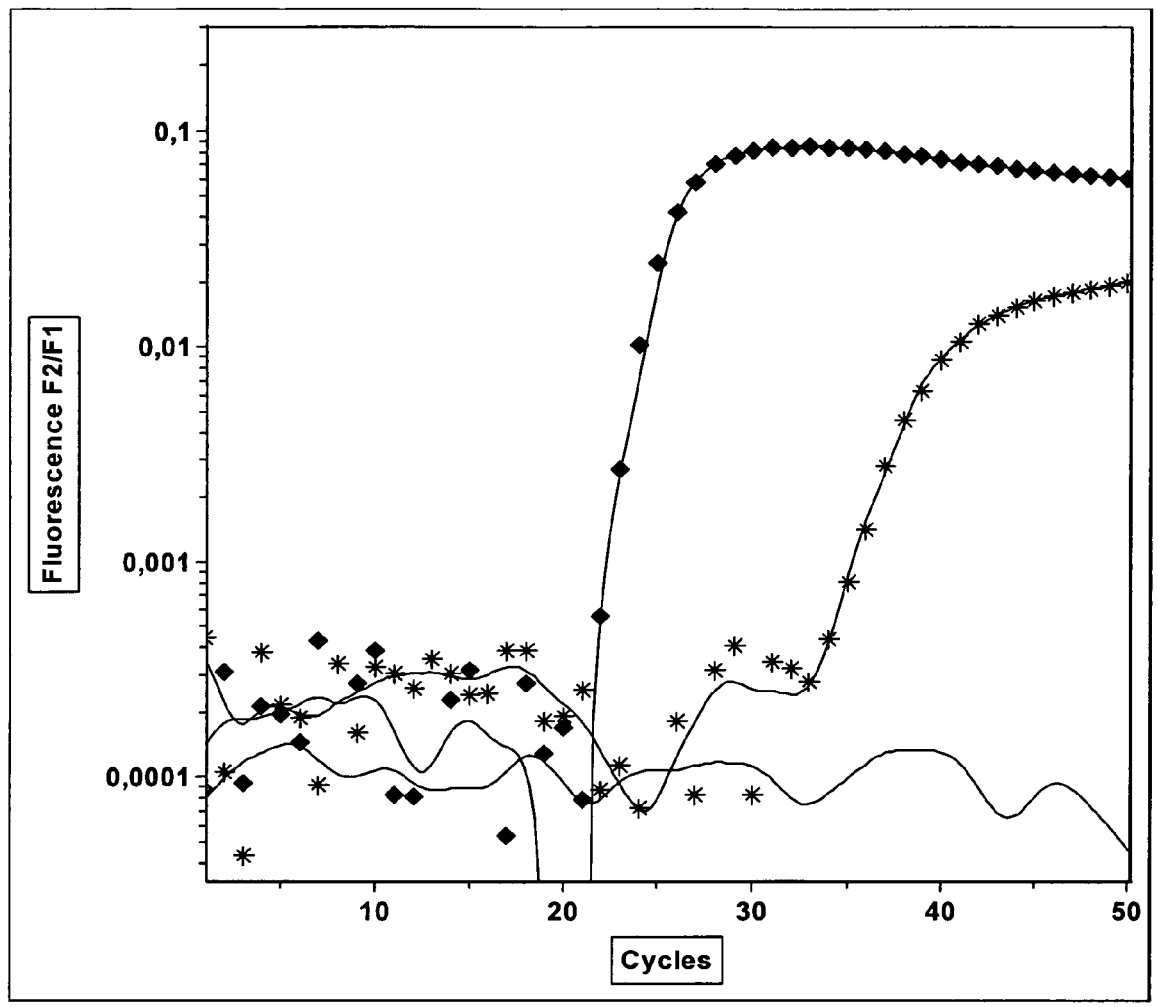
FIG. 4 demonstrates of the efficient degradation of uracil containing DNA. The plot shows the reamplification of PCR products containing uracil. The Y-axis shows the fluorescence signal measured in channel F2 normalized against channel F1 at each cycle (X-axis); $10^5$ copies were added to the reaction. The signals determined from reaction without Uracil-DNA-glycosylase are labeled diamonds showing a high efficient reamplification. The reaction containing Uracil-DNA-glycosylases results in dramatically increased crossing points (labeled in stars) indicating a strong degradation of uracil containing PCR products by UNG. No template control is marked as solid line.

As a control for the UNG activity $10^5$ copies of a uracil containing PCR product were added to the reaction premix, generated by use of the same primers but under presence of dUTP instead of dTTP. Reamplification took place when UNG was absent, with the expected efficiency of a crossing point of 22,6. However when UNG was present in the PCR-mix the crossing points reached only a value of 35,8 (FIG. 4). This difference demonstrates nicely the efficient degradation of PCR products by UNG resulting from the cleavage of uracils out of the DNA. In this example it was shown that desulfonated conventionally bisulfite treated DNA is also degraded by UNG (FIG. 2). However, not desulfonated bisulfite treated DNA does not work as substrate for UNG and serves—even after preincubation with UNG—as working template in an amplification reaction (FIG. 3).

In the Example the desulfonation of template DNA required for the successful amplification took place during the initial denaturing phase of the PCR reaction at 95° C. Only precondition for this step is an alkaline pH, such as given in the utilized PCR buffer. Simultaneously the UNG activity is terminated and is hence not capable of cleaving or degrading newly generated PCR product anymore.

In this Example three different concentrations (10 ng, 0.1 ng and 0.1 ng) of each desulfonated and sulfonated (containing 6-sulfonated 5,6-dihydro-uracils) DNA were used as templates in two different Hot-Start PCR reactions.

In one case the reaction mix contained 0.2 Units UNG, in the other case no UNG was added. PCR reactions were performed in the LightCycler™ in 20 μl reaction volume and contained:

10 μl of template DNA (in different concentrations)
2 μl of FastStart LightCycler™ Mix for Hybridization probes (Roche Diagnostics)
3.5 mM $MgCl_2$ (Roche Diagnostics)
0.30 μM forward primer (SEQ ID NO:1, TIB-MolBiol)
0.30 μM reverse primer (SEQ ID NO:2, TIB-MolBiol)
0.15 μM Probe1 (SEQ ID NO:3, TIB-MolBiol)
0.15 μM Probe2 (SEQ ID NO:4, TIB-MolBiol)
optional 0.2 Unit Uracil-DNA-Glycosylase (Roche Diagnostics)

The temperature-time-profile was programmed as follows:
Pre-incubation (UNG active) 15 min by 25° C.
Activation of polymerase: 20 min by 95° C.
50 temperature cycles: 10 sec by 95° C.
30 sec at 56° C.
10 sec at 72° C.
Finally the reaction is cooled down to 35° C.

The primers (SEQ ID NO:1, SEQ ID NO:2) used amplify a 123 bp long fragment of the GSTP1 gene (SEQ ID NO:5, nt 1184 to nt 1304 in Genbank Accession X08058). By utilizing sequence specific hybridization probes (SeqID 3, SEQ ID NO:4) the amplification rate was detected in a Real Time PCR. Data interpretation was carried out via the LightCycler Software in channel F2/F1.

The crossing point (Cp) was generated automatically by employing the method "Second Derivative Maximum" (Table 1).

RESULTS. The results of the experiment are summarized in Table 1. The reamplification of $10^5$ copies of uracil containing amplicons results in CT of 22,6 without UNG and 35,8 with UNG. The CT delay of 13 cycles demonstrates the efficient degradation of uracil containing template by the glycosylase. Also desulfonated bisulfite converted DNA was degraded by UNG and no amplification was measurable in the reaction with UNG. In the reaction without UNG the 10,1, and 0,1 ng DNA was detected at CT of 28,5/31,7/33,8. In contrast to this, sulfonated DNA, prepared according to the invention, was amplified in both cases, without and with Uracil-DNA-Glycosylase with almost the same efficiency and were detected at CT of 29,3/32,2/34,1 and 29,9/32,7/34,8 respectively.

TABLE 1

| DNA | Template DNA in ng | Crossing point of reaction without UNG | Crossing point of reaction with 0.2 Unit UNG added |
|---|---|---|---|
| PCR Amplicons containing Uracil | $10^5$ copies | 22.6 | 35.8 |
| desulfonated DNA | 10 | 28.5 | no signal |
|  | 1 | 31.7 | no signal |
|  | 0.1 | 33.8 | no signal |

TABLE 1-continued

| DNA | Template DNA in ng | Crossing point of reaction without UNG | Crossing point of reaction with 0.2 Unit UNG added |
|---|---|---|---|
| sulfonated DNA | 10 | 29.3 | 29.9 |
| | 1 | 32.2 | 32.7 |
| | 0.1 | 34.1 | 34.8 |

TABLE 2

Sequences of Oligonucleotides

| SeqID | Name | Sequence |
|---|---|---|
| SEQ ID NO: 1 | GSTP1.10F1 | GGGAttAtttTTATAAGGtT |
| SEQ ID NO: 2 | GSTP1.10R5 | TaCTaaaAaCTCTaAaCCCCATC |
| SEQ ID NO: 3 | GSTP1.10-fluo1 | TTCGtCGtCGtAGTtTTCGtt-Fluo |
| SEQ ID NO: 4 | GSTP1.10-red 1 | red640-tAGTGAGTACGCGCGGtt-PH |
| Seq ID NO: 5 | GSTP1 amplicon | 5'GGGAttAtttTTATAAGGtTCGGAG GtCGCGAGGttTTCGtTGGAGTTTCGt CGtCGtAGTtTTCGttAttAGTGAGTA CGCGCGGttCGCGTtttCGGGGATGGG GtTtAGAGtTtttAGtA |

Fluo=fluoresceine label, red640=LightCycler™ fluorescence label for channel F2, PH=3'OH-Phosphorylation. Small written t's point to converted cytosines by bisulfite treatment, respectively small a's point to the complementary adenosine bases in the reverse complement synthesized strand.

EXAMPLE 2

(The Stability of the Sulfonated Nucleic Bases in the Presence of UNG Activity was Analyzed When Stored at 4° C. or 40° C.)

In this experiment the stability of the sulfonated nucleic bases in the presence of UNG activity was analyzed when stored at 4° C. or 40° C. Again, two nucleic acid samples, containing 1.5 µg GpGenome™ Universal Methylated DNA (Chemicon International) diluted in 100 µl water were mixed with 354 µl of bisulfite solution (5.89 mol/l) and 146 µl of dioxane containing a radical scavenger (6-hydroxy-2,5,7,8-tetramethylchromane 2-carboxylic acid, 98.6 mg in 2.5 ml of dioxane). The reaction mixture was denatured for 3 min at 99° C. and subsequently incubated with the following temperature program for a total of 5 h: 30 min at 50° C.; a first thermospike (99.9° C.) for 3 min; 1.5 h at 50° C.; a second thermospike (99.9° C) for 3 min; 3 h at 50° C. One of the reaction mixtures served as a control whereas the other was treated according to the invention. The reaction mixtures of both the control and the test reaction were subsequently purified by ultrafiltration by means of a Millipore Microcon column. The purification was conducted essentially according to the manufacturer's instructions. For this purpose, the reaction mixture was mixed with 200 µl of water, loaded onto the ultrafiltration membrane, centrifuged for 15 min and subsequently washed with water. The DNA remains on the membrane in this treatment. For the control sample an alkaline desulfonation was performed according to the methods, which are state of the art (see for example US 20040152080, 20040115663, WO 2004/067545) (named 'desulfonated' in table 3). For this purpose, 100 µl of a 0.2 mol/l NaOH was added and incubated for 10 min. For the other sample this desulfonation step was replaced by adding 100 µl water (named 'sulfonated' in table 3). A centrifugation (10 min) was then conducted, followed by a final washing step with water. After this, the DNA was eluted. For this purpose, the membrane was mixed for 10 minutes with 50 µl of warm 1×TE buffer (50° C.) adjusted to pH7. The membrane was turned over according to the manufacturer's instructions. Subsequently a repeated centrifugation was conducted, with which the DNA was removed from the membrane.

Subsequently the DNA was divided in aliquots and some of them were stored at 4° C. for 12 h, others at 4° C. for 144 h and then used as template in a PCR reaction. To show the robustness of the method according to the invention applicants wanted to analyze whether this protecting effect of sulfonation would be stable over a period of time. The PCR reaction was performed under the same conditions.

In addition aliquots were stored at an increased temperature of 40° C. for 22 h and then used as template in a PCR reaction.

By stopping the chemical reaction after sulfonation the unmethylated cytosines were converted into C6 sulfonated uracils (5,6-Dihydro-6-sulfonyl-uracil) and methylated cytosines remained unchanged. However after a complete desulfonation, as described in the art, all unmethylated cytosines would have converted into uracil instead and methylated cytosines remain unchanged.

As a control for the UNG activity $10^5$ copies of a uracil containing PCR product were added to the reaction premix, generated by use of the same primers but under presence of dUTP instead of dTTP. Reamplification took place when UNG was absent, with the expected efficiency of a crossing point of 22,6. However, when UNG was present in the PCR-mix the crossing points reached only a value of 35,1 (Table 3). This difference demonstrates nicely the efficient degradation of PCR products by UNG resulting from the cleavage of uracils out of the DNA.

In this Example it was shown that bisulfite treated DNA which is not desulfonated according to the invention is stable at 4° C. for a longer period of at least 144 hrs. In addition it was shown that even storage at 40° C. for a period of 22 hrs does not have a major effect on the UNG protecting effect of sulfonation at C6-uracils.

TABLE 3

| | Template DNA in ng | Crossing point of reaction without UNG | Crossing point of reaction with 0.2 Unit UNG added |
|---|---|---|---|
| DNA after 12 h at 4° C. | | | |
| PCR amplicons containing uracil | $10^5$ copies | 22.6 | 35.8 |
| desulfonated DNA | 0.1 | 33.8 | no signal |
| sulfonated DNA | 0.1 | 34.1 | 34.8 |
| DNA after 144 h at 4° C. | | | |
| PCR amplicons containing uracil | 10.00E5 copies | 22.6 | 35.1 |
| desulfonated DNA | 10 | 28.3 | no signal |

TABLE 3-continued

|  | Template DNA in ng | Crossing point of reaction without UNG | Crossing point of reaction with 0.2 Unit UNG added |
|---|---|---|---|
| desulfonated DNA | 1 | 30.8 | no signal |
| desulfonated DNA | 0.1 | 33.5 | no signal |
| sulfonated DNA | 10 | 28.7 | 29.5 |
| sulfonated DNA | 1 | 31.7 | 31.8 |
| sulfonated DNA DNA after 22 h at 40° C. | 0.1 | 33.7 | 34.2 |
| PCR amplicons containing uracil | 10.00E5 copies | 22.6 | 35.7 |
| desulfonated DNA | 10 | 29.5 | no signal |
| desulfonated DNA | 1 | 32.5 | no signal |
| desulfonated DNA | 0.1 | 34.9 | no signal |
| sulfonated DNA | 10 | 29.5 | 30.5 |
| sulfonated DNA | 1 | 32.5 | 33.3 |
| sulfonated DNA | 0.1 | 34.6 | 36.1 |

EXAMPLE 3

(Comparison of Particular Inventive Methods with the Standard Workflow by Means of the Determination of the Methylation Rate of the TPEF Gene (Also Known as TMEFF2) in Colon Cancer Tissue)

1 µg of genomic DNA (200 µl) was extracted from tumours and normal adjacent tissue of 12 patients with colon cancer, respectively. The 24 samples obtained in this way were each divided into 2×100 µl DNA. 100 µl of each sample was treated according to standard procedures (bisulfite treatment protocol A, sample set A) or to the method according to the invention (bisulfite protocol B, sample set B). In between the DNA was stored at −20° C.

Standard Workflow:

Sample Set A:

Measurement of the DNA was performed according to the C3 quantification assay version A and according to the HeavyMethyl™ assay for the TPEF gene version A. A standard A was generated for calibration.

Generation of Standard A:

5 tubes each with 2 µg universal methylated DNA were treated with bisulfite according to the bisulfite treatment protocol A and pooled afterwards. The concentration of the DNA in solution was determined by means of UV at 260 nm after the bisulfite reaction.

Bisulfite Treatment Protocol A (Standard Procedures):

100 µl of the samples (sample set A) containing 0.5 µg DNA diluted in 100 µl water were mixed with 354 µl of bisulfite solution (5.89 mol/l) and 146 µl of dioxane containing a scavenger (6-hydroxy-2,5,7,8-tetramethylchromane 2-carboxylic acid, 98.6 mg in 2.5 ml of dioxane). The reaction mixture was denatured for 3 min at 99° C. and subsequently incubated with the following temperature program for a total of 5 h: 30 min 50° C.; one thermospike 99.9° C. for 3 min; 1.5 h 50° C; one thermospike 99.9° C. for 3 min; 3 h 50° C. The DNA of the reaction mixtures was subsequently purified by ultrafiltration by means of a Millipore Microcon column. The purification was conducted essentially according to the manufacturer's instructions. For this purpose, the reaction mixture was mixed with 200 µl of water, loaded onto the ultrafiltration membrane, centrifuged for 15 min and subsequently washed with water. The DNA remains on the membrane in this treatment. For complete desulfonation 100 µl of a 0.2 mol/l NaOH solution was added and incubated for 10 min. A centrifugation for 10 min was then conducted, followed by a final washing step with water. After this, the DNA was eluted. For this purpose, the membrane was mixed for 10 minutes with 75 µl of prewarmed 1×TE buffer (50° C.) adjusted to pH 8.5. Then the membrane was turned over and centrifuged according to the manufacturer's instructions to recover the DNA from the membrane.

C3 quantification assay:

The C3 quantification assay is a quantification assay specific for the total amount of bisulfite converted DNA. The assay amplifies a fragment of DNA that comprises multiple cytosine (but not CpG) positions in the genomic form, which are initially converted to uracil and during amplification replaced by thymine in the bisulfite converted variant. Accordingly the assay does not quantify for unconverted or partially converted bisulfite treated DNA (i.e. wherein the target sequence comprises one or more cytosine positions which have not been converted to thymine). The quantity of DNA in the sample is deduced by comparison of the measured CP (crossing point, which represents the threshold cycle) to a standard curve relating such CP values to DNA amounts. The standard curve is based on measurements of known quantities of bisulfite converted DNA with the according assay.

C3 Quantification Assay Version A:

A 20 µl reaction mixture contained:
2 µl of template DNA
2 µl of FastStart LightCycler™ Mix for hybridisation probes (Roche Diagnostics)
3.5 mmol/l $MgCl_2$ (Roche Diagnostics)
0.60 µmol/l forward primer SEQ ID NO:6, TIB-MolBiol)
0.60 µmol/l reverse primer (SEQ ID NO:7, TIB-MolBiol)
0.2 µmol/l probe 1 (SEQ ID NO:8, TIB-MolBiol)

The assay was performed according to the following temperature-time-profile:
activation 10 min at 95° C.
50 cycles: 10 sec at 95° C.
30 sec at 56° C.
10 sec at 72° C.

The used primers (SEQ ID NO:6 and SEQ ID NO:7) amplify a fragment of 123 bp of the GSTP1 gene (SEQ ID NO:9. nucleotide 2273 to nucleotide 2402 of GenBank Accession Number X08058). The detection was carried out during the annealing phase at 56° C. in channel F1 at 530 nm. The crossing points (CP) were calculated according to the "second derivative maximum" method by means of the LightCycler™ software.

Detection of the Methylation Rate According to the HeavyMethyl™ Assay for the TPEF Gene Version A:

A 20 µl reaction mixture contained:
2 µl of template DNA
2 µl of FastStart LightCycler™ Mix for hybridization probes (Roche Diagnostics)
3.5 mmol/l $MgCl_2$ (Roche Diagnostics)
0.30 µmol/l forward primer (SEQ ID NO:10, TIB-MolBiol)
0.30 µmol/l reverse primer (SEQ ID NO:11, TIB-MolBiol)

4.0 µmol/l blocker (SEQ ID NO:12, TIB-MolBiol)
0.15 µmol/l hybridization probe (SEQ ID NO:13, TIB-MolBiol)
0.15 µmol/l hybridization probe (SEQ ID NO:14, TIB-MolBiol)

The assay was performed according to the following temperature-time-profile:
activation 10 min at 95° C.
50 cycles: 10 sec at 95° C.
30 sec at 56° C.
10 sec at 72° C.

The used primers (SEQ ID NO:10 and SEQ ID NO:11) amplify a fragment of 113 bp of the TPEF gene (SEQ ID NO:15. nucleotide 1102 to nucleotide 1214 of GenBank Accession Number AF242221). The detection was carried out during the annealing phase at 56° C. in channel F2/F1 at 640/530 nm. The crossing points (CP) were calculated according to the "second derivative maximum" method by means of the LightCycler™ software.

Calculation of DNA Amounts from CP:

Both the C3 quantification assay and HeavyMethyl assay for the TPEF gene are Real Time PCR assays using an external standard for calculating the DNA amount of the measured samples. The absolute value (ng) for an unknown concentration is obtained by a comparison of the amplification of DNA in an unknown sample against a standard curve prepared with known concentrations of the same target. The standard samples are amplified in separate capillaries but within the same LightCycler™ run. The standard curve is the linear regression line through the data points on a plot of crossing points (threshold cycle) versus logarithm of standard sample concentration. The absolute amount of DNA (ng) of the unknown sample matches the data point of the standard curve at which the CP of the unknown sample fits the standard curve.

TABLE 4

Sequence of Oligonucleotides

| SeqID | Name | Sequence |
| --- | --- | --- |
| SEQ ID NO: 6 | C3F | GGAGTGGAGGAAAtTGAGAt |
| SEQ ID NO: 7 | C3R | CCACACAaCAaaTaCTCAaAaC |
| SEQ ID NO: 8 | C3-TAQ | FAMTGGGTGTTTGTAATTTTTGTTTTG TGTTAGGTT-BHQ1 |
| SEQ ID NO: 9 | C3-amplicon | GGAGTGGAGGAAAtTGAGAtttAtTGA GGTTACGTAGTTTGtttAAGGTtAAGt tTGGGTGttTGtAATtTTTGttttTGTG ttAGGtTGttTtttAGGTGTtAGGTGA GtTtTGAGtAttTGtTGTGTGG |
| SEQ ID NO: 10 | TPEF-61S | aAAAaAaAAAaaCTCCTCTaCATAC |
| SEQ ID NO: 11 | TPEF-62S | GGTtAtTGttTGGGttAAtAAATG |
| SEQ ID NO: 12 | TPEF-6B2 | aCATACaCCaCaaaTaaaTTaCCaaaA aCATCaaCCaa-PH |
| SEQ ID NO: 13 | TPEF-6SF1 | tTttttTTttCGGACGtCGtT-Fluo |
| SEQ ID NO: 14 | TPEF-6SR1 | red640-tCGGtCGATGtTttCGGtA A-PH |
| SEQ ID NO: 15 | TPEF-amplicon | GGTtAtTGttTGGGttAAtAAATGGAG ttCGtTtTttttTTttCGGACGTCGtT GttCGGtCGATGtTttCGGtAAtttAt tCGCGGCGTATGtAGAGGAGttTTTtT tTTTt |

Fluo=fluoresceine label, red640=LightCycler fluorescence label for channel F2, PH=3'OH-Phosphorylation, FAM=5'-FAM label, BHQ1=BlackHoleQuencher1. Small written t's point to converted cytosines by bisulfite treatment, respectively small a's point to the complementary adenosine bases in the reverse complement synthesized strand.

Exemplary Method According to the Invention:

Sample Set B:

Measurement of the DNA was performed according to the C3 quantification assay version B and according to the HeavyMethyl assay for the TPEF gene version B in addition of 10,000 copies of a PCR product of methylated DNA. A standard B (C6 sulfonated uracil containing DNA) was generated for calibration.

Generation of Standard B (C6 Sulfonated Uracil Containing DNA):

5 tubes each with 2.0 µg universal methylated DNA were treated with bisulfite according to the bisulfite treatment protocol B. The concentration of the DNA in solution was determined by means of UV at 260 nm after the bisulfite reaction.

Generation of PCR Products.

10 ng methylated bisulfite converted DNA generated according to standard procedures (bisulfite protocol A) were amplified by means of the HeavyMethyl assay for the TPEF gene version A. The PCR products were purified with the QIAquick PCR Purification Kit and subsequently analyzed on a 2% agarose gel. After this, a serial dilution was carried out with water to a final dilution of 1:10$^{10}$. 2 µl of this dilution was reamplified and quantificated according to the HeavyMethyl™ assay for the TPEF gene version A. The copy number was determined: 2 µl of the said dilution contain 10,000 copies of PCR product.

Bisulfite Treatment Protocol B (Protocol for Carry Over Protection):

100 µl of the samples (sample set B) containing 0.5 µg DNA diluted in 100 µl water were mixed with 354 µl of bisulfite solution (5.89 mol/l) and 146 µl of dioxane containing a scavenger (6-hydroxy-2,5,7,8-tetramethylchromane 2-carboxylic acid, 98.6 mg in 2.5 ml of dioxane). The reaction mixture was denatured for 3 min at 99° C. and subsequently incubated with the following temperature program for a total of 5 h: 30 min 50° C.; one thermospike 99.9° C. for 3 min; 1.5 h 50° C.; one thermospike 99.9° C. for 3 min; 3 h 50° C. The DNA of the reaction mixtures was subsequently purified by ultrafiltration by means of a Millipore Microcon column. The purification was conducted essentially according to the manufacturer's instructions. For this purpose, the reaction mixture was mixed with 200 µl of water, loaded onto the ultrafiltration membrane, centrifuged for 15 min and subsequently washed with water. The DNA remains on the membrane in this treatment. In contrast to the bisulfite treatment protocol A the DNA was not incubated with NaOH, but additionally washed with water. After this, the DNA was eluted. For this purpose, the membrane was mixed for 10 minutes with 75 µl of prewarmed water (50° C.). Then the membrane was turned over and centrifuged according to the manufacturer's instructions to recover the DNA from the membrane.

C3 Quantification Assay Version B:
A 20 µl reaction mixture contained:
2 µl of template DNA
2 µl PCR product (10,000 copies)
2 µl of FastStart LightCycler™ Mix for hybridization probes (Roche Diagnostics)

3.5 mmol/l MgCl$_2$ (Roche Diagnostics)
0.60 µmol/l forward primer (SEQ ID NO:6, TIB-MolBiol)
0.60 µmol/l reverse primer (SEQ ID NO:7, TIB-MolBiol)
0.2 µmol/l probe 1 (SEQ ID NO:8, TIB-MolBiol)
0.2 units uracil-DNA-glycosylase (Roche Diagnostics)

The assay was performed according to the following temperature-time-profile:
preincubation 10 min at 37° C.
desulfonation/activation 30 min at 95° C.
50 cycles: 10 sec at 95° C.
30 sec at 56° C.
10 sec at 72° C.

The used primers (SEQ ID NO:6 and SEQ ID NO:7) amplify a fragment of 123 bp of the GSTP1 gene (SEQ ID NO:9. nucleotide 2273 to nucleotide 2402 of GenBank Accession Number X08058). The detection was carried out during the annealing phase at 56° C. in channel F1 at 530 nm. The crossing points (CP) were calculated according to the "second derivative maximum" method by means of the LightCycler™ software.

Detection of the Methylation Rate According to the HeavyMethyl™ Assay for the TPEF Gene Version B:

A 20 µl reaction mixture contained:
2 µl of template DNA
2 µl PCR product (10,000 copies)
2 µl of FastStart LightCycler™ Mix for hybridisation probes (Roche Diagnostics)
3.5 mmol/l MgCl$_2$ (Roche Diagnostics)
0.30 µmol/l forward primer (SEQ ID NO:10, TIB-MolBiol)
0.30 µmol/l reverse primer (SEQ ID NO:11, TIB-MolBiol)
4.0 µmol/l blocker (SEQ ID NO:12, TIB-MolBiol)
0.15 µmol/l hybridisation probe (SEQ ID NO:13, TIB-MolBiol)
0.15 µmol/l hybridisation probe (SEQ ID NO:14, TIB-MolBiol)
0.2 units uracil-DNA-glycosylase (Roche Diagnostics)

The assay was performed according to the following temperature-time-profil:
preincubation 10 min at 37° C.
desulfonation/activation 30 min at 95° C.
50 cycles: 10 sec at 95° C.
30 sec at 56° C.
10 sec at 72° C.

The used primers (SEQ ID NO:10 and SEQ ID NO:11) amplify a fragment of 113 bp of the TPEF gene (SEQ ID NO:15, nucleotide 1102 to nucleotide 1214 of GenBank Accession Number AF242221). The detection was carried out during the annealing phase at 56° C. in channel F2/F1 at 640/530 nm. The crossing points (CP) were calculated according to the "second derivative maximum" method by means of the LightCycler™ software.

Calculation of DNA Amounts from CP:

Both the C3 quantification assay and HeavyMethyl™ assay for the TPEF gene are Real Time PCR assays using an external standard for calculating the DNA amount of the measured samples. The absolute value (ng) for an unknown concentration is obtained by a comparison of the amplification of DNA in an unknown sample against a standard curve prepared with known concentrations of the same target. The standard samples are amplified in separate capillaries but within the same LightCycler™ run. The standard curve is the linear regression line through the data points on a plot of crossing points (threshold cycle) versus logarithm of standard sample concentration. The absolute amount of DNA (ng) of the unknown sample matches the data point of the standard curve at which the CP of the unknown sample fits the standard curve.

Calculation of the methylation rate from DNA amounts: The results of the study are presented as methylation rates of the promotor region of the TPEF gene. According to the PMR value method ( Eads CA et al. Cancer Res., 61:3410-8, 2001. PMID: 11309301) the methylation rate is equal to the percentage of methylated copies measured in a sample as proportion of the total DNA measured in the same sample. In table 5 and 6 all CPs received from the C3 and the TPEF assay and the resulting DNA amounts are listed. In the right column the methylation rate (PMR) is shown, which was calculated from the DNA amounts listed in colums before.

Results:

TABLE 5

Results from the standard workflow. Colon cancer and normal adjacent tissue samples were bisulfite treated with bisulfite treatment protocol A followed by quantification with the C3 quantification assay version A using a calibration curve made by means of standard A. The table shows the crossing points and the calculated DNA amount of 2 replicates. The HeavyMethyl ™ assay for the TPEF gene version A detects only methylated DNA from the promoter region of TPEF gene. The table shows the measured CP values of 2 replicates and the calculated DNA amount. Finally the methylation percentages (PMR) were calculated by the ratio of methylated DNA and total DNA.

| Sample | Type | C3 Quantification Assay Version A | | | HeavyMethyl Assay TPEF gene Version B | | | |
|---|---|---|---|---|---|---|---|---|
| | | CP 1$^{st}$ run | CP 2$^{nd}$ run | ng/PCR mean | CP 1$^{st}$ run | CP 2$^{nd}$ run | ng/PCR mean | PMR % |
| standard A | 20 ng | 25.86 | 25.64 | | 26.28 | 26.55 | | |
| standard A | 5 ng | 28.29 | 27.72 | | 28.51 | 28.24 | | |
| standard A | 5 ng | 28.44 | 27.74 | | 28.51 | 28.15 | | |
| standard A | 1.25 ng | 30.27 | 30.2 | | 29.91 | 30.46 | | |
| standard A | 1.25 ng | 30.23 | 30.41 | | 29.92 | 30.21 | | |
| standard A | 0.31 ng | 32.48 | 32.01 | | 31.46 | 31.51 | | |
| standard A | 0.31 ng | 31.89 | 32.18 | | 31.13 | 31.54 | | |
| 1 | normal | 31.49 | 32.6 | 0.4 | 27.27 | 28.68 | 7.4 | 5% |
| 2 | tumor | — | — | 0.0 | 28.22 | 29.49 | 4.1 | 0% |
| 3 | normal | 32.74 | 33.56 | 0.1 | 27.84 | 28.97 | 5.4 | 2% |

TABLE 5-continued

Results from the standard workflow. Colon cancer and normal adjacent tissue samples were bisulfite treated with bisulfite treatment protocol A followed by quantification with the C3 quantification assay version A using a calibration curve made by means of standard A. The table shows the crossing points and the calculated DNA amount of 2 replicates. The HeavyMethyl ™ assay for the TPEF gene version A detects only methylated DNA from the promoter region of TPEF gene. The table shows the measured CP values of 2 replicates and the calculated DNA amount. Finally the methylation percentages (PMR) were calculated by the ratio of methylated DNA and total DNA.

| Sample | Type | C3 Quantification Assay Version A | | | HeavyMethyl Assay TPEF gene Version B | | | PMR % |
|---|---|---|---|---|---|---|---|---|
| | | CP $1^{st}$ run | CP $2^{nd}$ run | ng/PCR mean | CP $1^{st}$ run | CP $2^{nd}$ run | ng/PCR mean | |
| 4 | tumor | 29.51 | 30.96 | 1.5 | 28.08 | 29.42 | 4.4 | 33% |
| 5 | normal | 31.97 | 33.03 | 0.3 | 27.72 | 29.09 | 5.6 | 5% |
| 6 | tumor | 27.8 | 29.65 | 4.0 | 27.45 | 29.16 | 6.2 | 65% |
| 7 | normal | 32.02 | 33.47 | 0.2 | 27.62 | 28.93 | 6.0 | 4% |
| 8 | tumor | 28.5 | 30.53 | 2.5 | 27.56 | 29.2 | 5.9 | 43% |
| 9 | normal | 32.47 | 33.8 | 0.1 | 28.06 | 29.13 | 4.7 | 3% |
| 10 | tumor | 29.87 | 31.17 | 1.2 | 27.91 | 29.07 | 5.1 | 23% |
| 11 | normal | 31.93 | 33.65 | 0.2 | 27.17 | 29.12 | 7.2 | 3% |
| 12 | tumor | 32.07 | 33.27 | 0.2 | 27.1 | 28.29 | 8.6 | 3% |
| 13 | normal | 31.45 | 33.41 | 0.3 | 27.52 | 28.61 | 6.7 | 5% |
| 14 | tumor | 29.87 | 30.64 | 1.3 | 27.83 | 28.44 | 6.2 | 22% |
| 15 | normal | 35.97 | 32.94 | 0.1 | 27.8 | 28.2 | 6.7 | 1% |
| 16 | tumor | 28.92 | 29.07 | 2.8 | 28.54 | 28.73 | 4.4 | 64% |
| 17 | normal | 32.49 | 34.58 | 0.1 | 27.98 | 29.45 | 4.6 | 3% |
| 18 | tumor | 27.05 | 27.93 | 7.5 | 27.16 | 28.08 | 8.8 | 84% |
| 19 | normal | 31.6 | 32.78 | 0.3 | 27.6 | 28.95 | 6.0 | 6% |
| 20 | tumor | 28.78 | 30.11 | 2.4 | 27.59 | 28.79 | 6.2 | 38% |
| 21 | normal | 35.23 | 35.88 | 0.0 | 28.07 | 29.32 | 4.5 | 0% |
| 22 | tumor | 35 | 36.93 | 0.0 | 27.91 | 29.08 | 5.1 | 0% |
| 23 | normal | 31.86 | 32.72 | 0.3 | 27.63 | 28.31 | 6.9 | 4% |
| 24 | tumor | 30.01 | 31.55 | 1.0 | 27.47 | 28.58 | 6.9 | 15% |
| neg. contr. | — | — | — | — | — | — | — | — |

TABLE 6

Results generated by the method according to the invention (carry over prevention). Colon cancer and normal adjacent tissue samples were bisulfite treated with bisulfite treatment protocol B resulting in C6 sulfonated uracil containing DNA. Total DNA was measured with the C3 quantification assay version B using a calibration curve made by means of standard B. The table shows the crossing points and the calculated DNA amount from 2 replicates. Before the measurement of the methylated DNA with the HeavyMethyl ™ Assay for the TPEF gene version B, the reactions were contaminated with 10,000 copies of the TPEF amplicon containing uracil instead of thymine. The table shows the measured CP of 2 replicates and the calculated DNA amount. Finally the methylation percentages (PMR) were calculated by the ratio of methylated DNA and total DNA.

| sample | type | C3 Quantification Assay Version B | | | HeavyMethyl Assay for the TPEF gene Version B | | | PMR % |
|---|---|---|---|---|---|---|---|---|
| | | CP $1^{st}$ Run | CP $2^{nd}$ Run | ng/PCR mean | CP $1^{st}$ Run | CP $2^{nd}$ Run | ng/PCR mean | |
| standard B | 20 ng | 27.73 | 27.29 | | 27.63 | 27.31 | | |
| standard B | 5 ng | 29.18 | 28.58 | | 28.82 | 28.62 | | |
| standard B | 5 ng | 29.18 | 28.89 | | 28.76 | 28.73 | | |
| standard B | 1.25 ng | 31.04 | 30.71 | | 30.57 | 30.05 | | |
| standard B | 1.25 ng | 31.08 | 30.51 | | 30.33 | 30.01 | | |
| standard B | 0.31 ng | 32.9 | 32.84 | | 31.87 | 31.46 | | |
| standard B | 0.31 ng | 32.78 | 32.65 | | 32.27 | 31.69 | | |
| 1 | normal | 33.84 | 33.49 | 0.2 | 28.13 | 28.16 | 9.8 | 2% |
| 2 | tumor | 37.54 | — | 0.0 | 28.53 | 29.14 | 5.3 | 0% |
| 3 | normal | 34.43 | 34.72 | 0.2 | 29.14 | 29.68 | 3.0 | 5% |
| 4 | tumor | 30.46 | 30.1 | 1.9 | 28.23 | 28.2 | 9.1 | 21% |
| 5 | normal | 34.17 | 32.89 | 0.2 | 28.7 | 28.92 | 5.2 | 4% |
| 6 | tumor | 29.23 | 28.69 | 5.6 | 27.87 | 27.83 | 13.1 | 43% |
| 7 | normal | 32.97 | 32.87 | 0.3 | 27.92 | 28.01 | 11.7 | 2% |
| 8 | tumor | 30.82 | 30.63 | 1.3 | 28.44 | 28.78 | 6.4 | 21% |
| 9 | normal | 33.87 | 33.55 | 0.2 | 28.43 | 28.59 | 6.9 | 3% |

TABLE 6-continued

Results generated by the method according to the invention (carry over prevention). Colon cancer and normal adjacent tissue samples were bisulfite treated with bisulfite treatment protocol B resulting in C6 sulfonated uracil containing DNA. Total DNA was measured with the C3 quantification assay version B using a calibration curve made by means of standard B. The table shows the crossing points and the calculated DNA amount from 2 replicates. Before the measurement of the methylated DNA with the HeavyMethyl ™ Assay for the TPEF gene version B, the reactions were contaminated with 10,000 copies of the TPEF amplicon containing uracil instead of thymine. The table shows the measured CP of 2 replicates and the calculated DNA amount. Finally the methylation percentages (PMR) were calculated by the ratio of methylated DNA and total DNA.

| | | C3 Quantification Assay Version B | | | HeavyMethyl Assay for the TPEF gene Version B | | | |
|---|---|---|---|---|---|---|---|---|
| sample | type | CP 1$^{st}$ Run | CP 2$^{nd}$ Run | ng/PCR mean | CP 1$^{st}$ Run | CP 2n$^{d}$ Run | ng/PCR mean | PMR % |
| 10 | tumor | 30.97 | 31.19 | 1.0 | 28.58 | 29.12 | 5.2 | 20% |
| 11 | normal | 33.14 | 33.53 | 0.2 | 28.11 | 28.2 | 9.7 | 3% |
| 12 | tumor | 33.13 | 33.66 | 0.2 | 27.69 | 28 | 13.5 | 2% |
| 13 | normal | 33.04 | 33.57 | 0.3 | 28.44 | 28.86 | 6.2 | 4% |
| 14 | tumor | 31.08 | 31.54 | 0.9 | 28.03 | 28.79 | 8.4 | 10% |
| 15 | normal | 33.09 | 33.6 | 0.2 | 28.03 | 28.54 | 9.0 | 3% |
| 16 | tumor | 29.74 | 29.78 | 3.0 | 28.59 | 28.95 | 5.5 | 54% |
| 17 | normal | 33.95 | 33.52 | 0.2 | 28.43 | 28.68 | 6.7 | 3% |
| 18 | tumor | 28.66 | 28.69 | 7.3 | 28.09 | 28.09 | 10.3 | 70% |
| 19 | normal | 33.01 | 34.08 | 0.2 | 28.11 | 28.2 | 9.7 | 3% |
| 20 | tumor | 30.03 | 30.71 | 1.9 | 28.19 | 28.17 | 9.5 | 20% |
| 21 | normal | 36.24 | 36.98 | 0.2 | 28.92 | 29.25 | 4.0 | 4% |
| 22 | tumor | 36.04 | 35.12 | 0.1 | 28.58 | 28.9 | 5.6 | 2% |
| 23 | normal | 33.79 | 33.77 | 0.2 | 28.1 | 28.43 | 9.0 | 2% |
| 24 | tumor | 31.89 | 32.2 | 0.5 | 28.69 | 29.09 | 4.9 | 10% |
| neg. contr. | — | — | — | — | — | — | — | |

Figure 5:
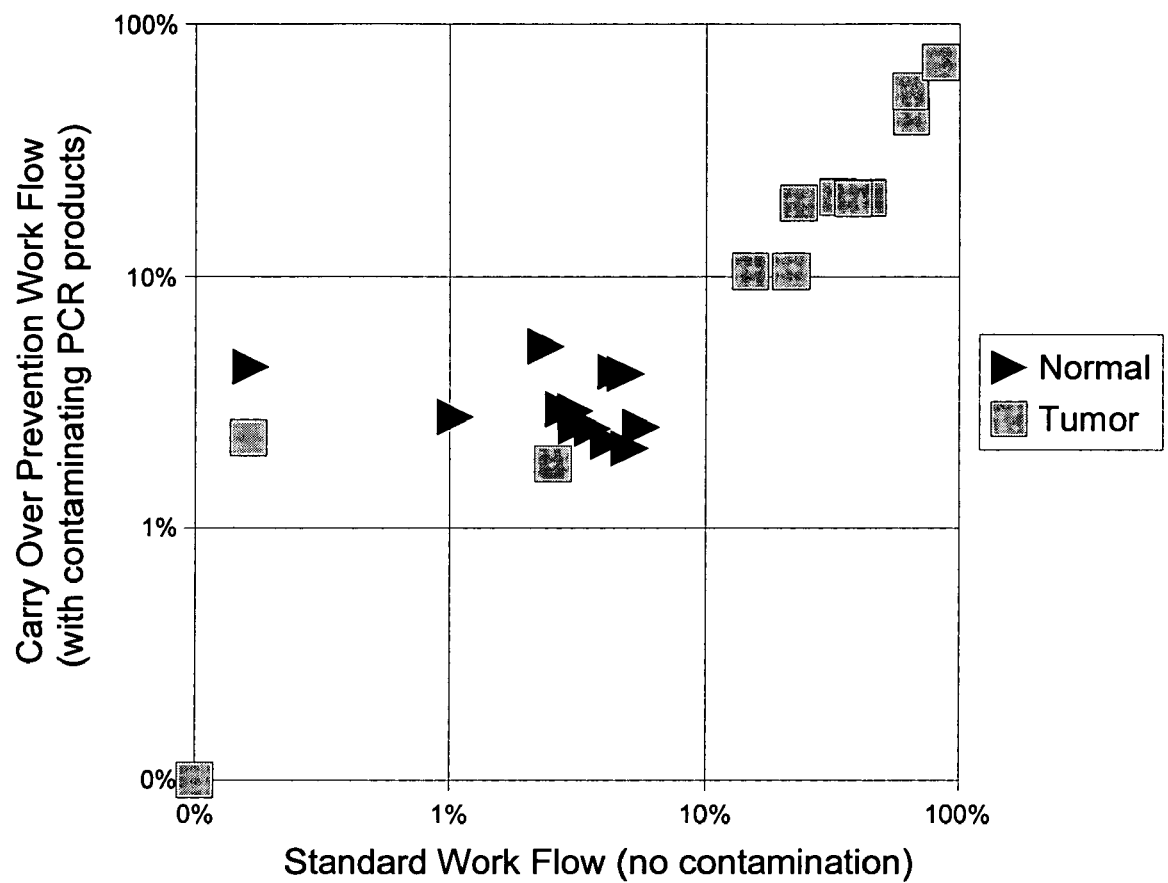
FIG. 5 shows a correlation plot of the results obtained in Example 3 by the standard workflow and the method according to the invention (carry over prevention). Every symbol represents a single sample: quadrates tumor tissues, triangles normal adjacent tissues. The percentage of methylation determined according to the standard workflow (x-axis) or to the method according to the invention (y-axis) is indicated for each sample. The exemplary inventive methods have led only in 2 out of 24 samples to a different methylation percentage as the standard workflow. This means that although the samples treated according to the method of the invention were contaminated with uracil containing TPEF amplicons, only DNA of the samples served as a template for amplification of the TPEF amplicon in nearly all cases. In case of the said two samples, the differing results occurred presumable because of the low methylation percentage of the DNA (smaller than 0.2%).

The results obtained by the standard workflow and the method according are compared in a correlation plot (FIG. 5). Every symbol represents a single sample: quadrates tumor tissues, triangles normal adjacent tissues. The percentage of methylation determined according to the standard workflow (x-axis) or to the method according to the invention (y-axis) is indicated for each sample.

The exemplary, representative method according to the invention have led only in 2 out of 24 samples to a different methylation percentage as the standard workflow. Although the samples treated according to the method of the invention were contaminated with uracil containing TPEF amplicons only DNA of the samples served as a template for amplification of the TPEF amplicon in nearly all cases. In case of the said two samples, the differing results occurred presumable because of the low methylation percentage of the DNA (smaller than 0.2%).

The invention claimed is:

1. A method for providing a decontaminated nucleic acid suitable for DNA 5-methylation analysis, comprising:
   a) contacting a DNA sample with a bisulfite reagent under conditions suitable to produce a bisulfite-treated sulfonated DNA sample, wherein unmethylated cytosines of the DNA are sulfonated, sulfonated and deaminated, or comprise a mixture of both forms, and wherein said sulfonated, or sulfonated and deaminated uracil has not been significantly desulfonated; and
   b) further contacting the bisulfite-treated sulfonated DNA sample with an amount of an enzyme that specifically degrades any contaminating nonsulfonated-uracil-containing nucleic acids and does not degrade sulfonated-uracil-containing nucleic acids thereby providing a decontaminated DNA sample suitable for DNA 5-methylation analysis.

2. The method of claim 1, wherein the contaminating nonsulfonated-uracil-containing nucleic acids comprise nonsulfonated-uracil-containing carry-over contaminants from a prior nucleic acid amplification reaction, and wherein the decontaminated DNA sample is thereby optimized for use in a subsequent amplification analysis.

3. The method of claim 2, wherein the subsequent amplification analysis comprises DNA methylation analysis.

4. The method of claim 1, further comprising:
   a) mixing the bisulfite-treated sulfonated DNA sample with at least one component required for a polymerase-mediated amplification reaction or an amplification-based detection assay;
   b) inactivating, after specifically degrading any nonsulfonated-uracil-containing nucleic acids, the specifically degrading enzymatic activity; and
   c) desulfonating, after said inactivating, the bisulfite-treated sulfonated DNA sample.

5. The method of claim 4, wherein inactivating and desulfonating occur simultaneously by incubating the mixture at an increased temperature, said incubation sufficient to inactivate the specifically degrading enzymatic activity, and desulfonate the bisulfite-treated sulfonated DNA.

6. The method of claim 4, further comprising, after desulfonating, amplifying the desulfonated DNA.

7. The method of claim 4, wherein the specifically degrading enzyme is at least one selected from the group consisting of a DNA glycosylase and an endonuclease.

8. The method of claim 7, wherein the DNA glycosylase is uracil-DNA-glycosylase (UNG).

9. The method of claim 4, further comprising, after inactivating and desulfonating, performing a polymerase-based amplification reaction or an amplification-based assay.

10. The method of claim 9, wherein the polymerase-based amplification reaction is initiated by a brief incubation at increased temperature, said incubation being sufficient to inactivate the specifically degrading enzymatic activity.

11. The method of claim 9, wherein the polymerase is a heat stable polymerase.

12. The method of claim 9, wherein the polymerase-mediated amplification, or the amplification-based assay is performed in the presence of dUTPs instead of dTTPs.

13. The method of claim 1, wherein the amount of the specifically degrading enzyme is sufficient to degrade substantially all of any nonsulfonated-uracil-containing nucleic acid contaminants and does not degrade sulfonated-uracil-contaiing nucleic acids.

14. A method for providing decontaminated nucleic acid suitable for methylation analysis, comprising bisulfite treatment of a nucleic acid sample to provide for a sulfonated nucleic acid sample; and contacting the bisulfite-treated sulfonated nucleic acid sample with uracil-DNA-glycosylase (UNG) under conditions suitable to specifically degrade any contaminating nonsulfonated-uracil-containing nucleic acids to provide for a decontaminated nucleic acid sample suitable for methylation analysis thereby providing a decontaminated nucleic acid sample suitable for DNA 5-methylation analysis.

* * * * *

SEQUENCE LISTING

<160> NUMBER OF SEQ ID NOS: 15

<210> SEQ ID NO 1
<211> LENGTH: 20
<212> TYPE: DNA
<213> ORGANISM: Artificial
<220> FEATURE:
<223> OTHER INFORMATION: GSTP1 forward primer

<400> SEQUENCE: 1
gggattattt ttataaggtt                                          20

<210> SEQ ID NO 2
<211> LENGTH: 23
<212> TYPE: DNA
<213> ORGANISM: Artificial
<220> FEATURE:
<223> OTHER INFORMATION: GSTP1 reverse  primer

<400> SEQUENCE: 2

-continued

```
tactaaaaac tctaaacccc atc                                           23

<210> SEQ ID NO 3
<211> LENGTH: 21
<212> TYPE: DNA
<213> ORGANISM: artificial sequence
<220> FEATURE:
<223> OTHER INFORMATION: GSTP1 probe

<400> SEQUENCE: 3
ttcgtcgtcg tagttttcgt t                                             21

<210> SEQ ID NO 4
<211> LENGTH: 18
<212> TYPE: DNA
<213> ORGANISM: artificial sequence
<220> FEATURE:
<223> OTHER INFORMATION: GSTP1 probe

<400> SEQUENCE: 4
tagtgagtac gcgcggtt                                                 18

<210> SEQ ID NO 5
<211> LENGTH: 123
<212> TYPE: DNA
<213> ORGANISM: artificial sequence
<220> FEATURE:
<223> OTHER INFORMATION: GSTP1 amplicon

<400> SEQUENCE: 5
gggattattt ttataaggtt cggaggtcgc gaggttttcg ttggagtttc gtcgtcgtag   60
ttttcgttat tagtgagtac gcgcggttcg cgttttcggg gatggggttt agagtttta   120 gta                                                                123

<210> SEQ ID NO 6
<211> LENGTH: 20
<212> TYPE: DNA
<213> ORGANISM: artificial sequence
<220> FEATURE:
<223> OTHER INFORMATION: C3 forward primer

<400> SEQUENCE: 6
ggagtggagg aaattgagat                                               20

<210> SEQ ID NO 7
<211> LENGTH: 22
<212> TYPE: DNA
<213> ORGANISM: artificial sequence
<220> FEATURE:
<223> OTHER INFORMATION: C3 reverse primer

<400> SEQUENCE: 7
ccacacaaca aatactcaaa ac                                            22

<210> SEQ ID NO 8
<211> LENGTH: 33
<212> TYPE: DNA
<213> ORGANISM: artificial sequence
<220> FEATURE:
<223> OTHER INFORMATION: C3 probe

<400> SEQUENCE: 8
tgggtgtttg taattttgt tttgtgttag gtt                                 33
```

```
<210> SEQ ID NO 9
<211> LENGTH: 130
<212> TYPE: DNA
<213> ORGANISM: artificial sequence
<220> FEATURE:
<223> OTHER INFORMATION: C3 amplicon

<400> SEQUENCE: 9
ggagtggagg aaattgagat ttattgaggt tacgtagttt gtttaaggtt aagtttgggt      60
gtttgtaatt tttgttttgt gttaggttgt tttttaggtg ttaggtgagt tttgagtatt     120
tgttgtgtgg                                                            130

<210> SEQ ID NO 10
<211> LENGTH: 25
<212> TYPE: DNA
<213> ORGANISM: artificial sequence
<220> FEATURE:
<223> OTHER INFORMATION: TPEF forward primer

<400> SEQUENCE: 10
aaaaaaaaaa aactcctcta catac                                            25

<210> SEQ ID NO 11
<211> LENGTH: 24
<212> TYPE: DNA
<213> ORGANISM: artificial sequence
<220> FEATURE:
<223> OTHER INFORMATION: TPEF reverse primer

<400> SEQUENCE: 11
ggttattgtt tgggttaata aatg                                             24

<210> SEQ ID NO 12
<211> LENGTH: 38
<212> TYPE: DNA
<213> ORGANISM: artificial sequence
<220> FEATURE:
<223> OTHER INFORMATION: TPEF blocker

<400> SEQUENCE: 12
acatacacca caaataaatt accaaaaaca tcaaccaa                              38

<210> SEQ ID NO 13
<211> LENGTH: 21
<212> TYPE: DNA
<213> ORGANISM: Artificial Sequence
<220> FEATURE:
<223> OTHER INFORMATION: TPEF probe

<400> SEQUENCE: 13
tttttttttt cggacgtcgt t                                                21

<210> SEQ ID NO 14
<211> LENGTH: 20
<212> TYPE: DNA
<213> ORGANISM: artificial sequence
<220> FEATURE:
<223> OTHER INFORMATION: TPEF probe

<400> SEQUENCE: 14
tcggtcgatg ttttcggtaa                                                  20

<210> SEQ ID NO 15
<211> LENGTH: 113
```

```
<212> TYPE: DNA
<213> ORGANISM: artificial sequence
<220> FEATURE:
<223> OTHER INFORMATION: TPEF amplicon

<400> SEQUENCE: 15
ggttattgtt tgggttaata aatggagttc gttttttttt tttcggacgt cgttgttcgg      60
tcgatgtttt cggtaattta ttcgcggcgt atgtagagga gttttttttt ttt           113
```